US012655161B2

(12) United States Patent
Arora et al.

(10) Patent No.: US 12,655,161 B2
(45) Date of Patent: Jun. 16, 2026

(54) SOLID FORMS OF AN EIF4E INHIBITOR

(71) Applicants: Pfizer Inc., New York, NY (US); EFFECTOR THERAPEUTICS, INC., Solana Beach, CA (US)

(72) Inventors: Kapildev Kashmirilal Arora, Niantic, CT (US); Wesley Dewitt Clark, Gales Ferry, CT (US); David Malcolm Crowe, Boothwyn, PA (US); Jason Gray, Boothwyn, PA (US)

(73) Assignees: Pfizer Inc., New York, NY (US); eFFECTOR Therapeutics Inc., Solana Beach, CA (US)

( * ) Notice: Subject to any disclaimer, the term of this patent is extended or adjusted under 35 U.S.C. 154(b) by 404 days.

(21) Appl. No.: 18/268,795

(22) PCT Filed: Dec. 22, 2021

(86) PCT No.: PCT/IB2021/062202
§ 371 (c)(1),
(2) Date: Jun. 21, 2023

(87) PCT Pub. No.: WO2022/137174
PCT Pub. Date: Jun. 30, 2022

(65) Prior Publication Data

US 2024/0076301 A1 Mar. 7, 2024

Related U.S. Application Data

(60) Provisional application No. 63/129,170, filed on Dec. 22, 2020.

(51) Int. Cl.
*C07D 519/00* (2006.01)

(52) U.S. Cl.
CPC .................................. *C07D 519/00* (2013.01)

(58) Field of Classification Search
CPC ..... C07D 519/00; C07D 495/04; A61P 35/00; A61K 31/519; C07B 2200/13
See application file for complete search history.

(56) References Cited

U.S. PATENT DOCUMENTS

| | | | | |
|---|---|---|---|---|
| 6,106,864 | A | 8/2000 | Dolan et al. | |
| 11,286,268 | B1 * | 3/2022 | Sperry | C07D 519/00 |
| 2015/0005340 | A1 | 1/2015 | Gong | |

FOREIGN PATENT DOCUMENTS

| | | | | |
|---|---|---|---|---|
| CN | 114269756 | A | 4/2022 | |
| WO | 0035298 | A1 | 6/2000 | |
| WO | 2014179237 | A1 | 11/2014 | |
| WO | WO-2021003157 | A1 * | 1/2021 | A61P 35/00 |
| WO | 2022137174 | A1 | 6/2022 | |

OTHER PUBLICATIONS

Hsieh, Clin. Cancer Res.; 16(20), 2010 (Year: 2010).*
Pettersson, Expert Opin. Ther. Targets, 2014, 18(9) (Year: 2014).*
Eisenhauer et al. (2009) "New Response Evaluation Criteria in Solid Tumours: Revised RECIST Guideline (version 1.1)", European Journal of Cancer, 45(2):228-247.
Giri et al. (2010) "Synthesis and Evaluation of Quinazolinone Derivatives as Inhibitors of NF-kappaB, AP-1 Mediated Transcription and eIF-4E Mediated Translational Activation: Inhibitors of Multi-Pathways Involve in Cancer", European Journal of Medicinal Chemistry, 45(9):3558-3563.
Liang et al. (2001) "Fast-Dissolving Intraoral Drug Delivery Systems", Expert Opinion on Therapeutic Patents, 11(6):981-986.
Liu et al. (Apr. 29, 2010) "Selective Inhibition of IDO1 Effectively Regulates Mediators of Antitumor Immunity", Blood, 115(17):3520-3530.
Rörsch et al. (Apr. 26, 2012) "Structure-Activity Relationship of Nonacidic Quinazolinone Inhibitors of Human Microsomal Prostaglandin Synthase 1 (mPGES 1)", Journal of Medicinal Chemistry, 55(8):3792-3803.
Terentis et al. (Dec. 15, 2009) "The Selenazal Drug Ebselen Potently Inhibits Indoleamine 2,3-Dioxygenase by Targeting Enzyme Cysteine Residues", Biochemistry, 49(3):591-600.
Verma et al. (2001) "Current Status of Drug Delivery Technologies and Future Directions", Pharmaceutical Technology On-Line, 25:1-14.

* cited by examiner

*Primary Examiner* — Susanna Moore
*Assistant Examiner* — Luisalberto Gonalez
(74) *Attorney, Agent, or Firm* — Mintz Levin Cohn Ferris Glovsky and Popeo, P.C.

(57) ABSTRACT

The present invention relates to solid forms of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide, to pharmaceutical compositions comprising such solid forms, and to methods of using such solid forms and pharmaceutical compositions for the treatment of cancer.

9 Claims, 10 Drawing Sheets

SOLID FORMS OF AN EIF4E INHIBITOR

FIELD OF THE INVENTION

The present invention relates to solid forms of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide, to pharmaceutical compositions comprising such solid forms, and to methods of using such solid forms and pharmaceutical compositions for the treatment of cancer.

BACKGROUND

The compound 7-(5-chloro-2-(3-(5-cyano-6-((1-(3,3-difluorocyclobutyl)piperidin-4-yl)(methyl)amino)-2-methyl-4-oxopyrido [3,4-d]pyrimidin-3(4H)-yl)prop-1-yn-1-yl)phenyl)-N-(methylsulfonyl)thieno[3,2-b]pyridine-3-carboxamide is an inhibitor of eukaryotic initiation factor 4e (eIF4e) represented by the Formula (I) below.

(I)

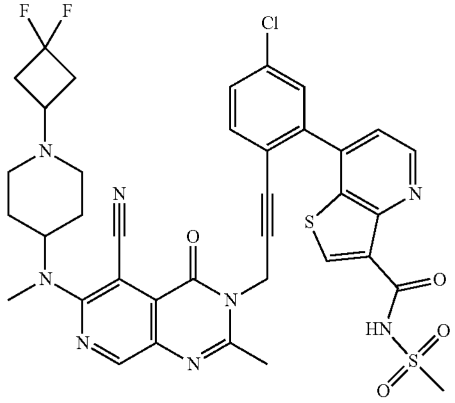

The preparation of 7-(5-chloro-2-(3-(5-cyano-6-((1-(3,3-difluorocyclobutyl)piperidin-4-yl)(methyl)amino)-2-methyl-4-oxopyrido [3,4-d]pyrimidin-3(4H)-yl)prop-1-yn-1-yl)phenyl)-N-(methylsulfonyl)thieno[3,2-b]pyridine-3-carboxamide is disclosed in Example 4A of the International Publication No. WO 2021/003157 A1 (see the depiction below), and the content is incorporated herein by reference in its entirety.

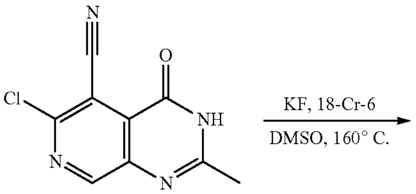

1

-continued

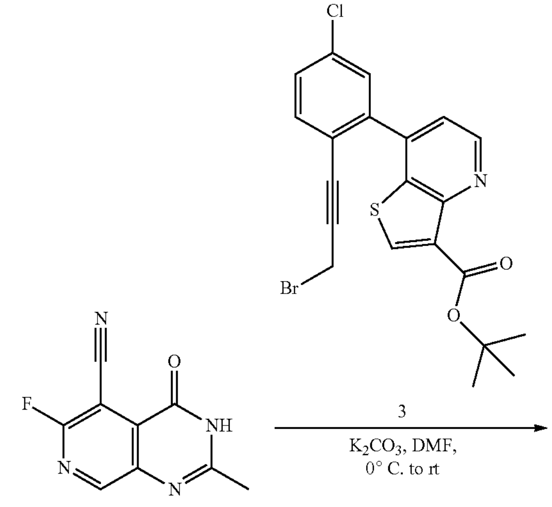

2

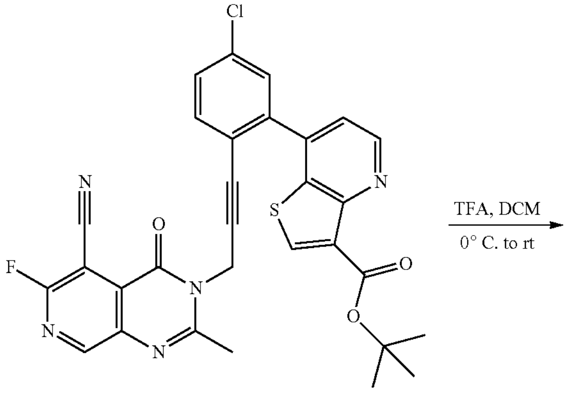

4

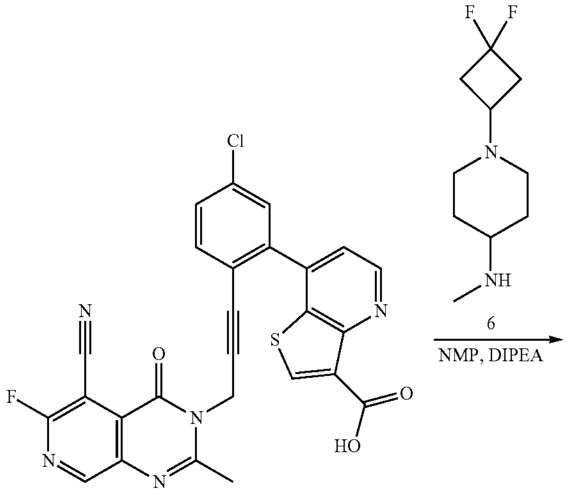

5

-continued

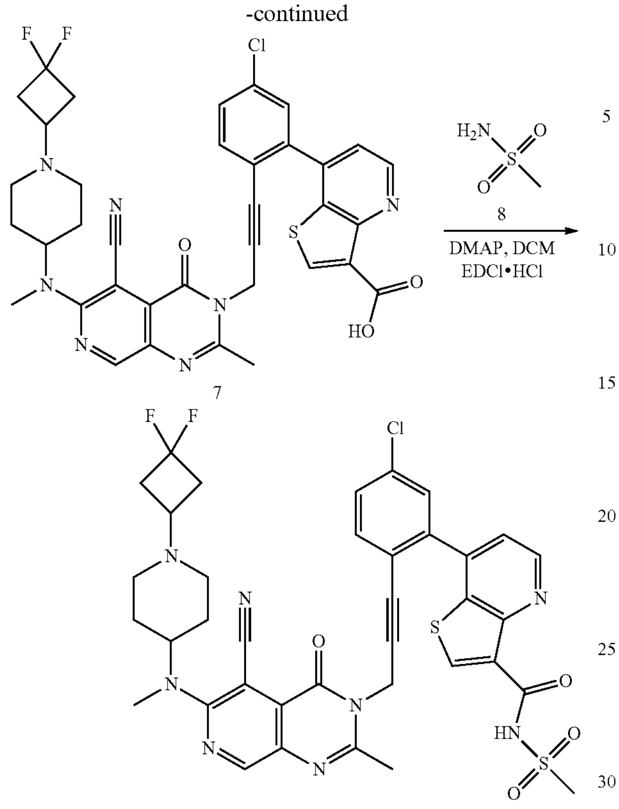

7

1188

In this procedure, the solution of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)thieno[3,2-b]pyridine-3-carboxylic acid (7, 1.70 g, 2.377 mmol) and methanesulfonamide (8, 0.564 g, 5.94 mmol) in dichloromethane (17.0 mL) were added with 1-ethyl-3-(3-dimethylaminopropyl) carbodiimide hydrochloride (0.737 g, 4.754 mmol) and 4-(dimethylamino) pyridine (0.725 g, 5.94 mmol) at 0° C. The reaction mixture was stirred at room temperature for 14 h. After completion, the reaction mixture was washed with 10% Citric acid (10 vol). The Organic layer was subsequently concentrated at atmospheric pressure down to a low volume (8 vol) where upon acetonitrile (12 vol) was charged. The organic mixture was concentrated at atmospheric pressure to a final volume (8 vol). The resultant yellow slurry was cooled to 40° C. where upon water was charged (2 vol) and the mixture cooled to 20° C. over 1 hr. The resultant slurry was held an additional 2 hrs at 20° C. followed by filtration to afford 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide as a yellow solid.

Eukaryotic initiation factor 4E (eIF4E) is a general translation factor, but it has the potential to enhance preferentially the translation of messenger RNAs (mRNAs) that lead to production of malignancy-associated proteins. This selectivity may relate to an increased requirement for eIF4E and its binding partners for the translation of mRNAs containing extensive secondary structure in their 5'-untranslated regions (5'-UTRs). These mRNAs include those encoding certain proteins that control cell cycle progression and tumorigenesis. Under normal cellular conditions, the translation of these malignancy-associated mRNAs is suppressed as the availability of active eIF4E is limited; however, their levels can increase when eIF4E is over-expressed or hyperactivated. Elevated levels of eIF4E have been found in many types of tumors and cancer cell lines including cancers of the colon, breast, bladder, lung, prostate, gastrointestinal tract, head and neck, Hodgkin's lymphomas, and neuroblastomas.

Accordingly, given its role in regulating regulation of cancer pathways, eIF4E is an attractive target for modulation with small molecule inhibitors such as 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Formula (I)). The present invention provides solid forms of Formula (I) having desirable properties including, but not limited to, stability, high crystallinity, high purity, high bio-performance, and manufacturability.

SUMMARY

The present invention provides solid forms of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Formula (I)). In some aspects and embodiments, the invention provides crystalline forms of Formula (I) hydrate (e.g., Form 1 and Form 2), as further described herein. In other aspects and embodiments, the invention provides an amorphous form of Formula (I), as further described herein.

In one aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having:

(1) a powder X-ray diffraction (PXRD) pattern (2θ) comprising: (a) one, two, three, four, five, or more than five peaks selected from the group consisting of the peaks in Table 1 in °2θ±0.2°2θ; or (b) peaks at 2θ values essentially the same as in FIG. 1;

(2) a Raman spectrum comprising: (a) one, two, three, four, five, or more than five wavenumber ($cm^{-1}$) values selected from the group consisting of the values in Table 2 in $cm^{-1}$±2 $cm^{-1}$; or (b) wavenumber ($cm^{-1}$) values essentially the same as in FIG. 2;

(3) a $^{13}C$ solid state NMR spectrum (ppm) comprising: (a) one, two, three, four, five, or more than five resonance (ppm) values selected from the group consisting of the values in Table 3 in ppm±0.2 ppm; or (b) resonance (ppm) values essentially the same as in FIG. 3; or (4) a $^{19}F$ solid state NMR spectrum (ppm) comprising: (a) one or two resonance (ppm) values selected from the group consisting of the values in Table 4 in ppm±0.2 ppm; or (b) resonance (ppm) values essentially the same as in FIG. 4;

or any combination of (1)(a)-(b), (2)(a)-(b), (3)(a)-(b), and (4)(a)-(b), provided they are not inconsistent with each other.

In another aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a powder X-ray diffraction (PXRD) pattern comprising peaks at 2θ values of: 7.8, 6.4, and 5.2° 2θ±0.2°2θ.

In another aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a Raman spectrum comprising wavenumber ($cm^{-1}$) values of: 1694 and 1680 $cm^{-1}$±2 $cm^{-1}$.

In another aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a $^{13}C$ solid state NMR spectrum comprising resonance (ppm) values of: 47.3, 125.4, and 153.6 ppm±0.2 ppm.

In another aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a $^{19}F$ solid state NMR spectrum comprising resonance (ppm) values of: −93.2 and −80.4 ppm±0.2 ppm.

In another aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), having: (a) a powder X-ray diffraction (PXRD) pattern comprising peaks at 2θ values of: 7.8, 6.4, and 5.2° 2θ±0.2° 2θ; (b) a Raman spectrum comprising wavenumber ($cm^{-1}$) values of: 1694 and 1680 $cm^{-1}$±2 $cm^{-1}$; (c) a $^{13}C$ solid state NMR spectrum comprising resonance (ppm) values of: 47.3, 125.4, and 153.6 ppm±0.2 ppm; or (d) a $^{19}F$ solid state NMR spectrum comprising resonance (ppm) values of: −93.2 and −80.4 ppm±0.2 ppm; or any combination of (a), (b), (c) and (d).

In another aspect, the invention provides a pharmaceutical composition comprising a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein, and a pharmaceutically acceptable carrier or excipient.

In another aspect, the invention provides a method of treating cancer in a subject in need thereof, comprising administering to the subject a therapeutically effective amount of the crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein.

In another aspect, the invention provides use of a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein, for the treatment of cancer.

In another aspect, the invention provides use of a pharmaceutical composition comprising a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein, for the treatment of cancer.

In yet another aspect, the invention provides use of a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein, in the manufacture of a medicament for the treatment of cancer.

In one aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 2) having: a powder X-ray diffraction (PXRD) pattern (2θ) comprising: (a) one, two, three, four, five, or more than five peaks selected from the group consisting of the peaks in Table 5 in °2θ±0.2°2θ; or (b) peaks at 2θ values essentially the same as in FIG. 5.

In another aspect, the invention provides an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) having:

(1) a powder X-ray diffraction (PXRD) pattern (2θ) comprising: one, two, three, four, five, or more than five peaks at 2θ values essentially the same as in FIG. 6;

(2) a Raman spectrum comprising: (a) one, two, three, four, five, or more than five wavenumber ($cm^{-1}$) values selected from the group consisting of the values in Table 6 in $cm^{-1}$±2 $cm^{-1}$; or (b) wavenumber ($cm^{-1}$) values essentially the same as in FIG. 7;

(3) a $^{13}C$ solid state NMR spectrum (ppm) comprising: (a) one, two, three, four, five, or more than five resonance (ppm) values selected from the group consisting of the values in Table 7 in ppm±0.2 ppm; or (b) resonance (ppm) values essentially the same as in FIG. 8; or (4) a $^{19}F$ solid state NMR spectrum (ppm) comprising: (a) one or two resonance (ppm) values selected from the group consisting of the values in Table 8 in ppm±0.2 ppm; or (b) resonance (ppm) values essentially the same as in FIG. 9;

or any combination of (1), (2)(a)-(b), (3)(a)-(b), and (4)(a)-(b), provided they are not inconsistent with each other.

In another aspect, the invention provides an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) having a Raman spectrum comprising wavenumber ($cm^{-1}$) values of: 1590, 1570, and 1519 $cm^{-1}$±2 $cm^{-1}$.

In another aspect, the invention provides an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) having a $^{13}C$ solid state NMR spectrum comprising resonance (ppm) values of: 152.4, 50.2, and 41.5 ppm±0.5 ppm.

In another aspect, the invention provides an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) having a $^{19}F$ solid state NMR spectrum comprising resonance (ppm) values of: −97.4 and −81.4 ppm±0.5 ppm.

In another aspect, the invention provides a pharmaceutical composition comprising an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein, and a pharmaceutically acceptable carrier or excipient.

In another aspect, the invention provides a method of treating cancer in a subject in need thereof, comprising administering to the subject a therapeutically effective amount of an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein.

In another aspect, the invention provides a method of treating cancer in a subject in need thereof, comprising administering to the subject a therapeutically effective amount of a pharmaceutical composition comprising an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein.

In another aspect, the invention provides use of an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein, for the treatment of cancer.

In another aspect, the invention provides use of a pharmaceutical composition comprising an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein, for the treatment of cancer.

In yet another aspect, the invention provides use of an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein, in the manufacture of a medicament for the treatment of cancer.

In another aspect, the invention provides a method of treating cancer in a subject in need thereof, comprising administering to the subject a therapeutically effective amount of a solid forms of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide as described herein, and further comprising administering another anti-cancer agent.

DETAILED DESCRIPTION

Figure 1:
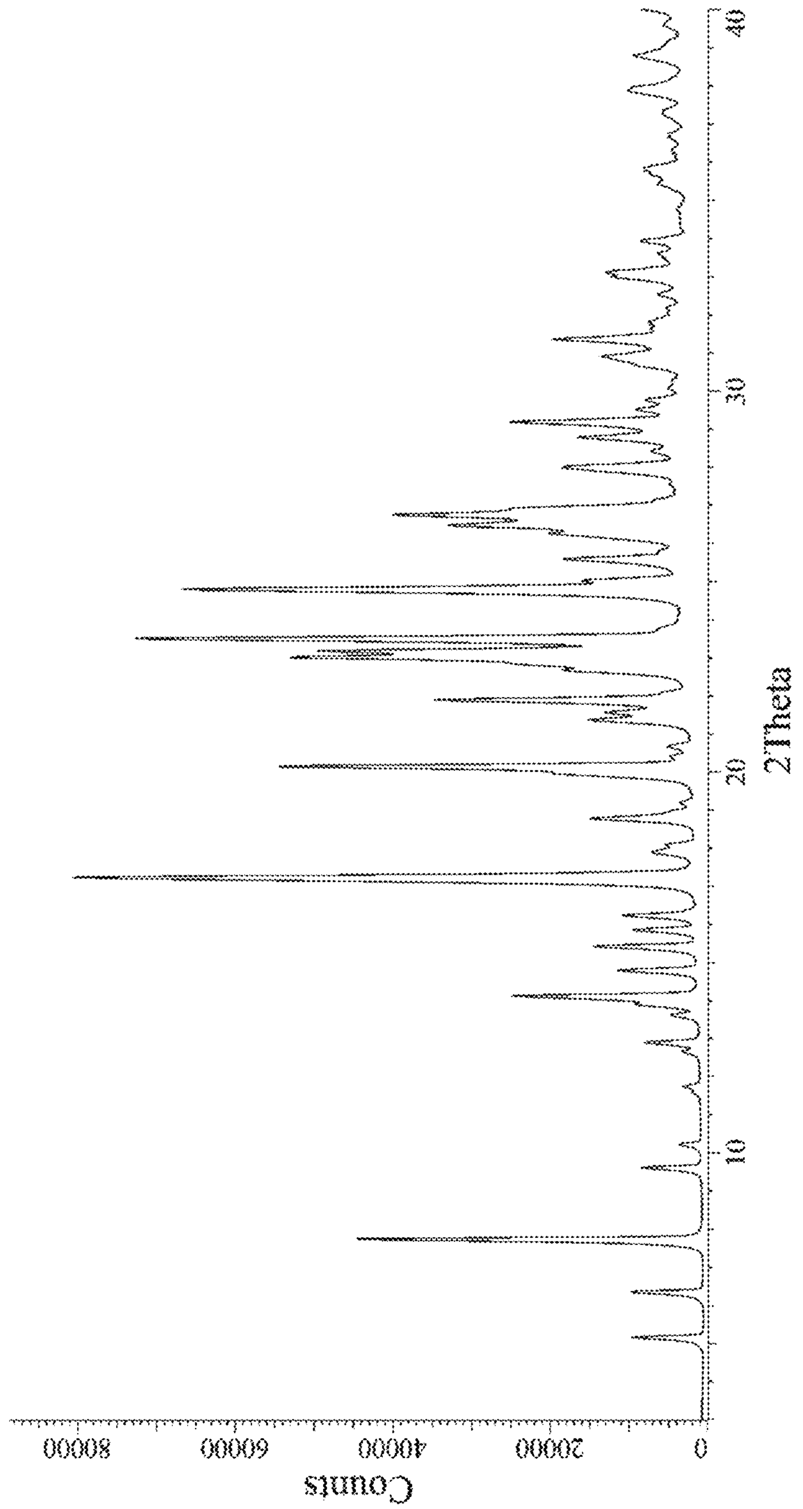
FIG. 1 shows the PXRD pattern of crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form1).

The present invention provides solid forms of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Formula (I)). In some aspects and embodiments, the invention provides crystalline forms of Formula (I) hydrate (e.g., Form 1 and Form 2), as further described herein. In other aspects and embodiments, the invention provides an amorphous form of Formula (I), as further described herein. The invention further provides pharmaceutical compositions comprising such solid forms, and methods of using such solid forms and pharmaceutical compositions for the treatment of cancer.

Definitions

As used herein, the singular form "a", "an", and "the" include plural references unless indicated otherwise. For example, "a" substituent includes one or more substituents.

The term "about" means having a value falling within an accepted standard of error of the mean, when considered by one of ordinary skill in the art, typically such as plus or minus (±) 10%, unless otherwise indicated.

As used herein, the term "essentially the same" means that variability typical for the particular method is taken into account. For example, with reference to powder X-ray diffraction (PXRD) peak positions, the term "essentially the same" means that typical variability in peak position and intensity are taken into account. One skilled in the art will appreciate that the peak positions (2θ) will show some variability, typically as much as ±0.2°. Further, one skilled in the art will appreciate that relative peak intensities will show inter-apparatus variability, as well as variability due to the degree of crystallinity, preferred orientation, prepared sample surface, and other factors known to those skilled in the art and should be taken as qualitative measures only. Similarly, Raman spectrum wavenumber ($cm^{-1}$) values show variability, typically as much as ±2 $cm^{-1}$, while $^{13}C$ and $^{19}F$ solid state NMR spectrum (ppm) show variability, typically as much as ±0.2 ppm.

The term "amorphous" as used herein, refers to a solid substance which (1) lacks order in three dimensions, or (2) exhibits order in less than three dimensions, order only over short distances (e.g., less than 10 Å), or both. Amorphous solids give diffuse PXRD patterns typically comprising one or two broad peaks.

The term "crystalline" as used herein, means having a regularly repeating arrangement of molecules or external face planes. Crystalline forms may differ with respect to thermodynamic stability, physical parameters, x-ray structure and preparation processes.

The terms "polymorph" or "polymorphic" refers to a crystalline form of a compound with a distinct spatial lattice arrangement as compared to other crystalline forms of the same compound.

The term "solvate" describes a molecular complex comprising a compound (e.g., the active pharmaceutical ingredient (API) of a drug product) and a stoichiometric or non-stoichiometric amount of one or more solvent molecules (e.g., water or ethanol). When the solvent is tightly bound to the compound, the resulting complex will have a well-defined stoichiometry that is independent of humidity. When, however, the solvent is weakly bound, as in channel solvates and hygroscopic compounds, the solvent content will be dependent on humidity and drying conditions. In such cases the complex will often be non-stoichiometric.

The term "hydrate" describes a solvate comprising the compound and a stoichiometric or non-stoichiometric amount of water.

The expression "substantially pure" means that the crystalline or amorphous form described as substantially pure comprises less than 5%, preferably less than 3%, and more preferably less than 1% by weight of impurities, including any other physical form of the compound.

"Tumor" as it applies to a subject diagnosed with, or suspected of having, a cancer refers to a malignant or potentially malignant neoplasm or tissue mass of any size and includes primary tumors and secondary neoplasms. A solid tumor is an abnormal growth or mass of tissue that usually does not contain cysts or liquid areas. Examples of solid tumors are sarcomas, carcinomas, and lymphomas. Leukaemia's (cancers of the blood) generally do not form solid tumors (National Cancer Institute, Dictionary of Cancer Terms).

"Tumor burden" or "tumor load', refers to the total amount of tumorous material distributed throughout the body. Tumor burden refers to the total number of cancer cells or the total size of tumor(s), throughout the body, including lymph nodes and bone marrow. Tumor burden can be determined by a variety of methods known in the art, such as, e.g., using calipers, or while in the body using imaging techniques, e.g., ultrasound, bone scan, computed tomography (CT), or magnetic resonance imaging (MRI) scans.

The term "tumor size" refers to the total size of the tumor which can be measured as the length and width of a tumor. Tumor size may be determined by a variety of methods known in the art, such as, e.g., by measuring the dimensions of tumor(s) upon removal from the subject, e.g., using calipers, or while in the body using imaging techniques, e.g., bone scan, ultrasound, CR or MRI scans.

The term "patient" or "subject" refer to any single subject for which therapy is desired or that is participating in a clinical trial, epidemiological study or used as a control, including humans and mammalian veterinary patients such as cattle, horses, dogs and cats. In some embodiments, the subject is a human.

The terms "treat" or "treating" of a cancer as used herein means to administer a compound of the present invention to a subject having cancer, or diagnosed with cancer, to achieve at least one positive therapeutic effect, such as, for example, reduced number of cancer cells, reduced tumor size, reduced rate of cancer cell infiltration into peripheral organs, or reduced rate of tumor metastases or tumor growth, reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

As used herein, the term "complete response" or "CR" means the disappearance of all signs of cancer (e.g., disappearance of all target lesions) in response to treatment. This does not always mean the cancer has been cured.

As used herein, the term "disease-free survival" (DFS) means the length of time after primary treatment for a cancer ends that the patient survives without any signs or symptoms of that cancer.

As used herein, the term "duration of response" (DoR) means the length of time that a tumor continues to respond to treatment without the cancer growing or spreading. Treatments that demonstrate improved DoR can produce a durable, meaningful delay in disease progression.

As used herein, the terms "objective response" and "overall response" refer to a measurable response, including complete response (CR) or partial response (PR). The term "overall response rate" (ORR) refers to the sum of the complete response (CR) rate and the partial response (PR) rate.

As used herein, the term "overall survival" (OS) means the length of time from either the date of diagnosis or the start of treatment for a disease, such as cancer, that patients diagnosed with the disease are still alive. OS is typically measured as the prolongation in life expectancy in patients who receive a certain treatment as compared to patients in a control group (i.e., taking either another drug or a placebo).

As used herein, the term "partial response" or "PR" refers to a decrease in the size of one or more tumors or lesions, or in the extent of cancer in the body, in response to treatment. For example, in some embodiments, PR refers to at least a 30% decrease in the sum of the longest diameters (SLD) of target lesions, taking as reference the baseline SLD.

As used herein, the term "progression free survival" or "PFS" refers to the length of time during and after treatment during which the disease being treated (e.g., cancer) does not get worse. PFS, also referred to as "Time to Tumor Progression", may include the amount of time patients have experienced a CR or PR, as well as the amount of time patients have experienced SD.

As used herein, the term "progressive disease" or "PD" refers to a cancer that is growing, spreading or getting worse. In some embodiments, PR refers to at least a 20% increase in the SLD of target lesions, taking as reference the smallest SLD recorded since the treatment started, or to the presence of one or more new lesions.

As used herein, the term "stable disease" (SD) refers to a cancer that is neither decreasing nor increasing in extent or severity.

As used herein, the term "sustained response" refers to the sustained effect on reducing tumor growth after cessation of a treatment. For example, the tumor size may be the same size or smaller as compared to the size at the beginning of the medicament administration phase. In some embodiments, the sustained response has a duration of at least the same as the treatment duration, at least 1.5×, 2×, 2.5×, or 3×length of the treatment duration, or longer.

The anti-cancer effect of the method of treating cancer, including "objective response," "complete response," "partial response," "progressive disease," "stable disease," "progression free survival," "duration of response," as used herein, may be defined and assessed by the investigators using RECIST v1.1 (Eisenhauer et al., New response evaluation criteria in solid tumors: Revised RECIST guideline (version 1.1), Eur J of Cancer, 2009; 45(2):228-47).

The terms "treatment regimen", "dosing protocol" and "dosing regimen" may be used interchangeably to refer to the dose and timing of administration of the crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) or the amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), as described herein, alone or in combination with an additional anticancer agent.

"Ameliorating" means reducing to some extent or improving one or more symptoms upon treatment with a compound or drug, such as the crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) or the amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), as described herein, as compared to not administering the compound. "Ameliorating" also includes shortening or reduction in duration of a symptom. That is, reducing to some extent, preferably, eliminating a symptom.

The present invention may be understood more readily by reference to the following detailed description of the embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

The invention described herein may be suitably practiced in the absence of any element(s) not specifically disclosed herein. Thus, for example, in each instance herein any of the terms "comprising", "consisting essentially of", and "consisting of" may be replaced with either of the other two terms.

Solid Forms

The crystalline and amorphous forms of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Formula (I)) described herein may be characterized by the following methods: (1) powder X-ray diffraction (PXRD) (2θ); (2) Raman spectroscopy ($cm^{-1}$); (3) $^{13}C$ solid state NMR spectroscopy (ppm); (4) $^{19}F$ solid state NMR spectroscopy (ppm); or any combination of methods (1), (2), (3), and (4).

In each of the aspects and embodiments herein that are characterized by PXRD, the PXRD peaks were collected using Cu$K\overline{\alpha}$ radiation at 1.5418λ.

Such solid forms may be further characterized by additional techniques, such as Fourier transform infrared spectroscopy (FTIR), thermogravimetric analysis (TGA), differential scanning calorimetry (DSC) (Tg ° C.), or differential thermal analysis (DTA).

Accordingly, in one aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1). In some embodiments, Form 1 is characterized by its powder X-ray diffraction (PXRD) pattern. In other embodiments, Form 1 is characterized by its Raman spectrum. In other embodiments, Form 1 is characterized by its $^{13}C$ solid state NMR spectrum. In still other embodiments, Form 1 is characterized by its $^{19}F$ solid state NMR spectrum.

In further embodiments, crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) is characterized by any combination of these methods. Exemplary combinations including two or more of the following are provided herein: powder X-ray diffraction (PXRD) pattern (2θ); Raman spectrum wavenumber values ($cm^{-1}$); $^{13}C$ solid state NMR spectrum (ppm); or $^{19}F$ solid state NMR spectrum (ppm). In some embodiments, crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) is characterized by PXRD and Raman. In other embodiments, crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) is characterized by PXRD and $^{13}C$ solid state NMR. In some embodiments, crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) is characterized by PXRD and $^{19}F$ solid state NMR. In some embodiments, crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) is characterized by $^{19}F$ solid state NMR and Raman. In some embodiments, crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) is characterized by $^{19}F$ solid state NMR and $^{13}C$ solid state NMR. In other embodiments, crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) is characterized by PXRD, Raman and $^{13}C$ solid state NMR. In some embodiments, crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) is characterized by PXRD, Raman and $^{19}F$ solid state NMR.

In one aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) characterized by a powder X-ray diffraction (PXRD) pattern.

In one embodiment, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a powder X-ray diffraction (PXRD) pattern comprising peaks at 2θ values of: 7.8, 6.4, and 5.2°2θ±0.2°2θ.

In one embodiment, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a powder X-ray diffraction (PXRD) pattern comprising peaks at 2θ values of: 7.8, 6.4, 5.2, and 17.2°2θ±0.2°2θ.

In another embodiment, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a PXRD pattern comprising: (a) one, two, three, four, five, or more than five peaks selected from the group consisting of the peaks in Table 1 in °2θ±0.2°2θ; or (b) peaks at 2θ values essentially the same as in FIG. 1.

In another aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) characterized by a Raman spectrum.

In one embodiment, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a Raman spectrum comprising wavenumber ($cm^{-1}$) values of: 1590, 1570, and 1519 $cm^{-1}$±2 $cm^{-1}$.

Figure 2:
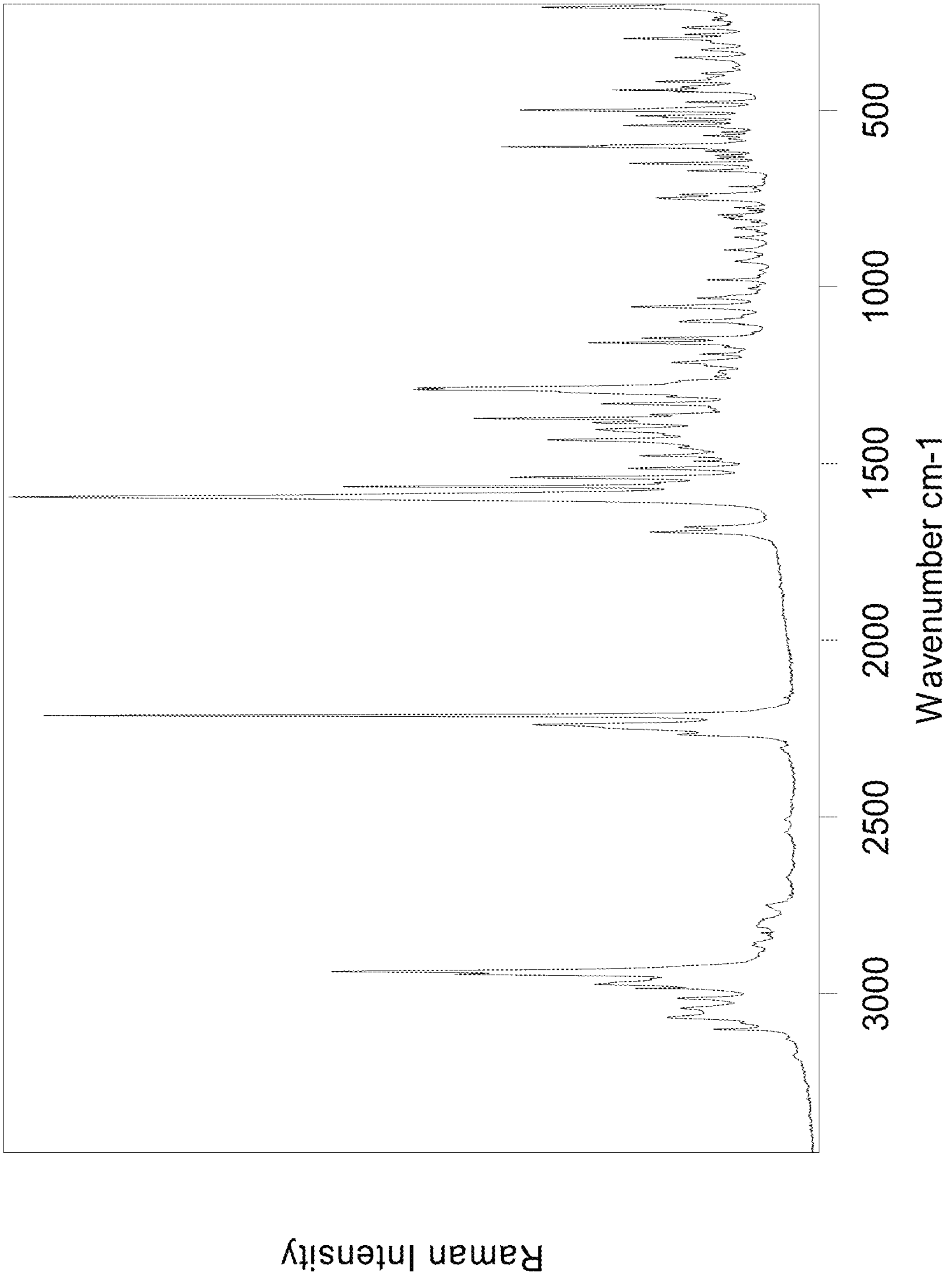
FIG. 2 shows the FT-Raman spectrum of crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form1).

In one embodiment, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a Raman spectrum comprising: (a) one, two, three, four, five, or more than five wavenumber ($cm^{-1}$) values selected from the group consisting of the values in Table 2 in $cm^{-1}$±2 $cm^{-1}$; or (b) wavenumber ($cm^{-1}$) values essentially the same as in FIG. 2.

In another aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) characterized by a $^{13}C$ solid state NMR spectrum.

In one embodiment, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a $^{13}C$ solid state NMR spectrum comprising resonance (ppm) values of: 47.3 ppm±0.2 ppm.

In one embodiment, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a $^{13}C$ solid state NMR spectrum comprising resonance (ppm) values of: 47.3 ppm±0.2 ppm; and one or two resonance (ppm) values selected from the group consisting of: 125.4 and 153.6 ppm±0.2 ppm.

In one embodiment, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a $^{13}C$ solid state NMR spectrum comprising resonance (ppm) values of: 47.3, 125.4, and 153.6 ppm±0.2 ppm.

Figure 3:
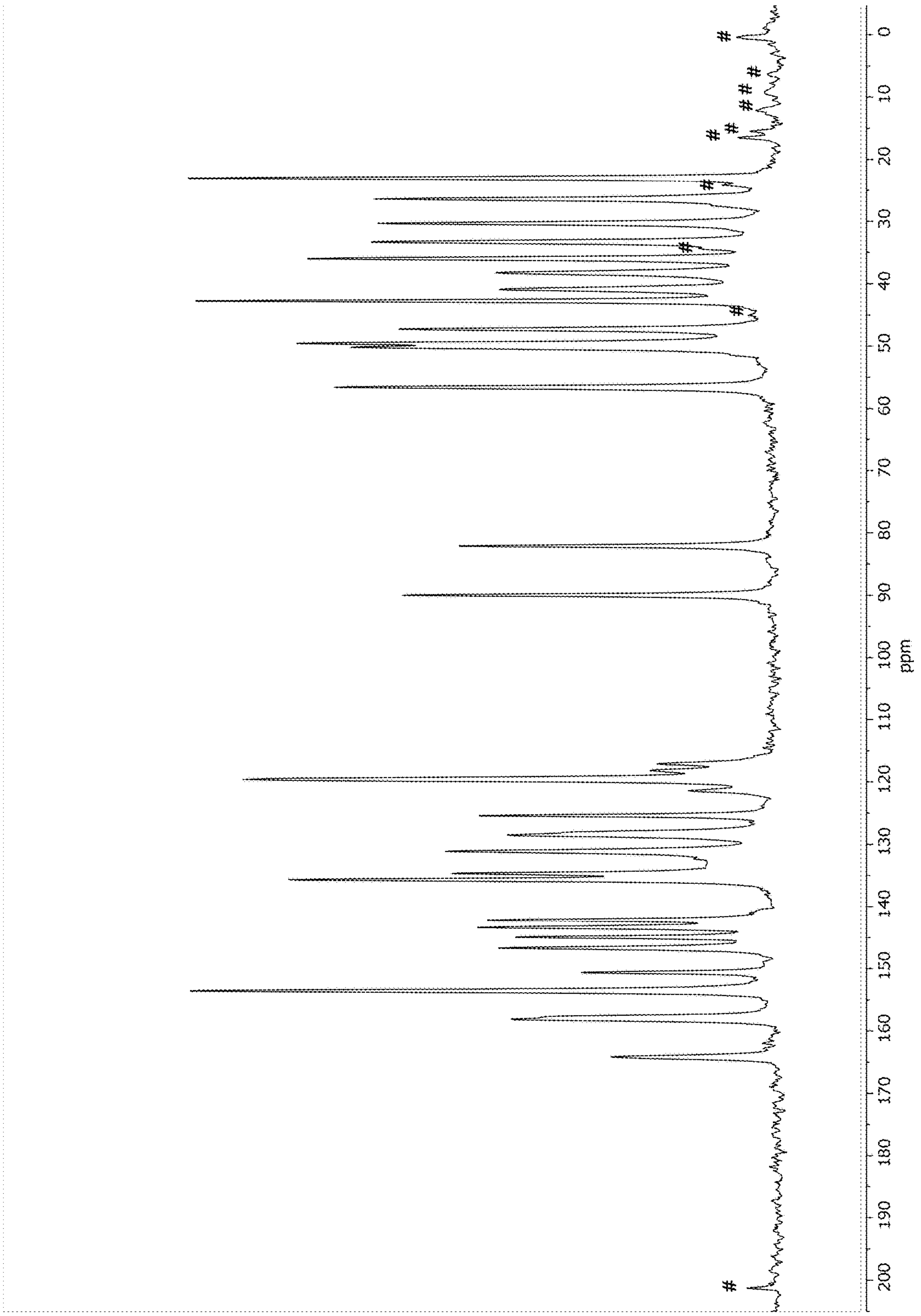
FIG. 3 shows the $^{13}C$ solid state NMR spectrum of crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form1). The peaks marked by hashes are spinning side bands.

In another embodiment, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a $^{13}C$ solid state NMR spectrum (ppm) comprising: (a) one, two, three, four, five, or more than five resonance (ppm) values selected from the group consisting of the values in Table 3 in ppm±0.2 ppm; or (b) resonance (ppm) values essentially the same as in FIG. 3.

In another aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) characterized by a $^{19}F$ solid state NMR spectrum.

In one embodiment, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a $^{19}F$ solid state NMR spectrum comprising a resonance (ppm) value of: −93.2 ppm±0.2 ppm.

In one embodiment, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a $^{19}F$ solid state NMR spectrum comprising resonance (ppm) values of: −93.2 and −80.4 ppm±0.2 ppm.

Figure 4:
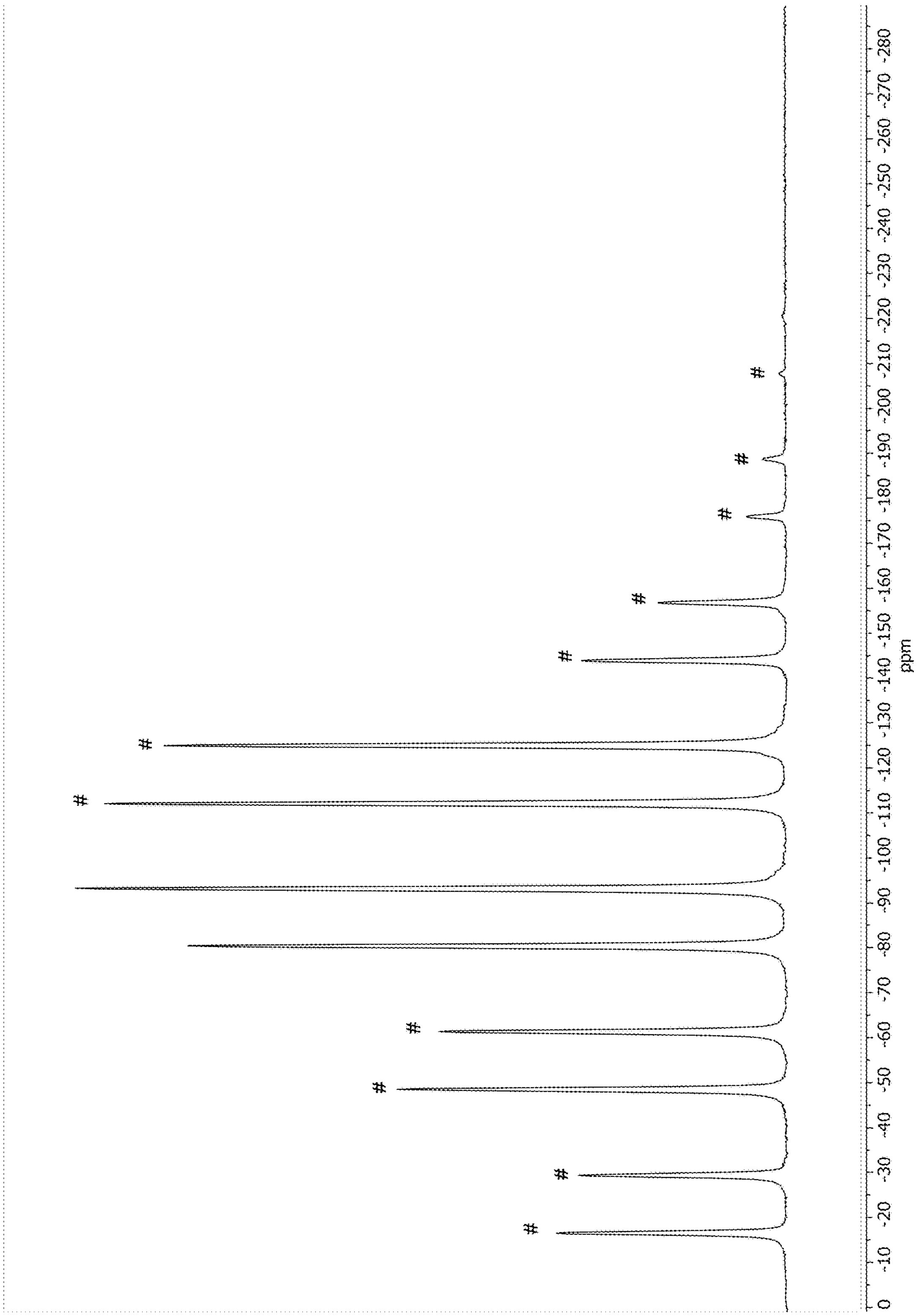
FIG. 4 shows the $^{19}F$ solid state NMR spectrum of crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form1). The peaks marked by hashes are spinning side bands.

In another embodiment, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a $^{19}F$ solid state NMR spectrum (ppm) comprising: (a) one or two resonance (ppm) values selected from the group consisting of the values in Table 4 in ppm±0.2 ppm; or (b) resonance (ppm) values essentially the same as in FIG. 4.

In another aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), having:

(a) a powder X-ray diffraction (PXRD) pattern comprising peaks at 2θ values of: 7.8, 6.4, and 5.2°2θ±0.2° 2θ;

(b) a Raman spectrum comprising wavenumber ($cm^{-1}$) values of: 1694 and 1680 $cm^{-1}$±2 $cm^{-1}$;

(c) a $^{13}C$ solid state NMR spectrum comprising resonance (ppm) values of: 47.3, 125.4, and 153.6 ppm±0.2 ppm; or (d) a $^{19}F$ solid state NMR spectrum comprising resonance (ppm) values of: −93.2 and −80.4 ppm±0.2 ppm; or any combination of (a), (b), (c) and (d).

In another aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), having:

(a) a powder X-ray diffraction (PXRD) pattern comprising peaks at 2θ values of: 7.8, 6.4, 5.2, and 17.2 020±0.2 020;

(b) a Raman spectrum comprising wavenumber ($cm^{-1}$) values of: 1694 and 1680 $cm^{-1}$±2 $cm^{-1}$;

(c) a $^{13}C$ solid state NMR spectrum comprising resonance (ppm) values of: 47.3, 125.4, and 153.6 ppm±0.2 ppm; or (d) a $^{19}F$ solid state NMR spectrum comprising resonance (ppm) values of: −93.2 and −80.4 ppm±0.2 ppm; or any combination of (a), (b), (c) and (d).

In another aspect, the invention provides a pharmaceutical composition comprising a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein, and a pharmaceutically acceptable carrier or excipient.

In another aspect, the invention provides a method of treating cancer in a subject in need thereof, comprising administering to the subject a therapeutically effective amount of a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein.

In another aspect, the invention provides a method of treating cancer in a subject in need thereof, comprising administering to the subject an amount of a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein, and an amount of an additional anticancer agent, wherein the amounts of Form 1 and the additional anticancer agent together are effective in treating cancer.

In another aspect, the invention provides a method of treating cancer in a subject in need thereof, comprising administering to the subject a therapeutically effective amount of a pharmaceutical composition comprising a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein.

In another aspect, the invention provides a method of treating cancer in a subject in need thereof, comprising administering to the subject an amount of a pharmaceutical composition comprising a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein, and an amount of an additional anticancer agent, wherein the amounts of Form 1 and the additional anticancer agent together are effective in treating cancer.

In another aspect, the invention provides use of a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3- carboxamide hydrate (Form 1), according to the aspects or embodiments described herein, for the treatment of cancer.

In another aspect, the invention provides use of a pharmaceutical composition comprising a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein, for the treatment of cancer.

In another aspect, the invention provides use of a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein, for use in the treatment of cancer.

In another aspect, the invention provides use of a pharmaceutical composition comprising a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein, for use in the treatment of cancer.

In yet another aspect, the invention provides use of a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein, in the manufacture of a medicament for the treatment of cancer.

In yet another aspect, the invention provides use of a pharmaceutical composition comprising a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), according to the aspects or embodiments described herein, in the manufacture of a medicament for the treatment of cancer.

In one aspect, the invention provides a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 2) having: a powder X-ray diffraction (PXRD) pattern (2θ) comprising: (a) one, two, three, four, five, or more than five peaks selected from the group consisting of the peaks in Table 5 in °2θ±0.2°2θ; or (b) peaks at 2θ values essentially the same as in FIG. 5.

In each of the aspects and embodiments of crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1 or 2) described herein, the crystalline form may be a substantially pure crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 1 or Form 2).

Each of the embodiments described herein for crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1 or 2) may be combined with other such embodiments, provided the embodiments are not inconsistent with each other.

In another aspect, the invention provides an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 3). In some embodiments, Form 3 is characterized by its powder X-ray diffraction (PXRD) pattern. In other embodiments, Form 3 is characterized by its Raman spectrum. In other embodiments, Form 3 is characterized by its $^{13}C$ solid state NMR spectrum. In still other embodiments, Form 3 is characterized by its $^{19}F$ solid state NMR spectrum. In further embodiments, Form 3 is characterized by any combination of these methods.

Figure 6:
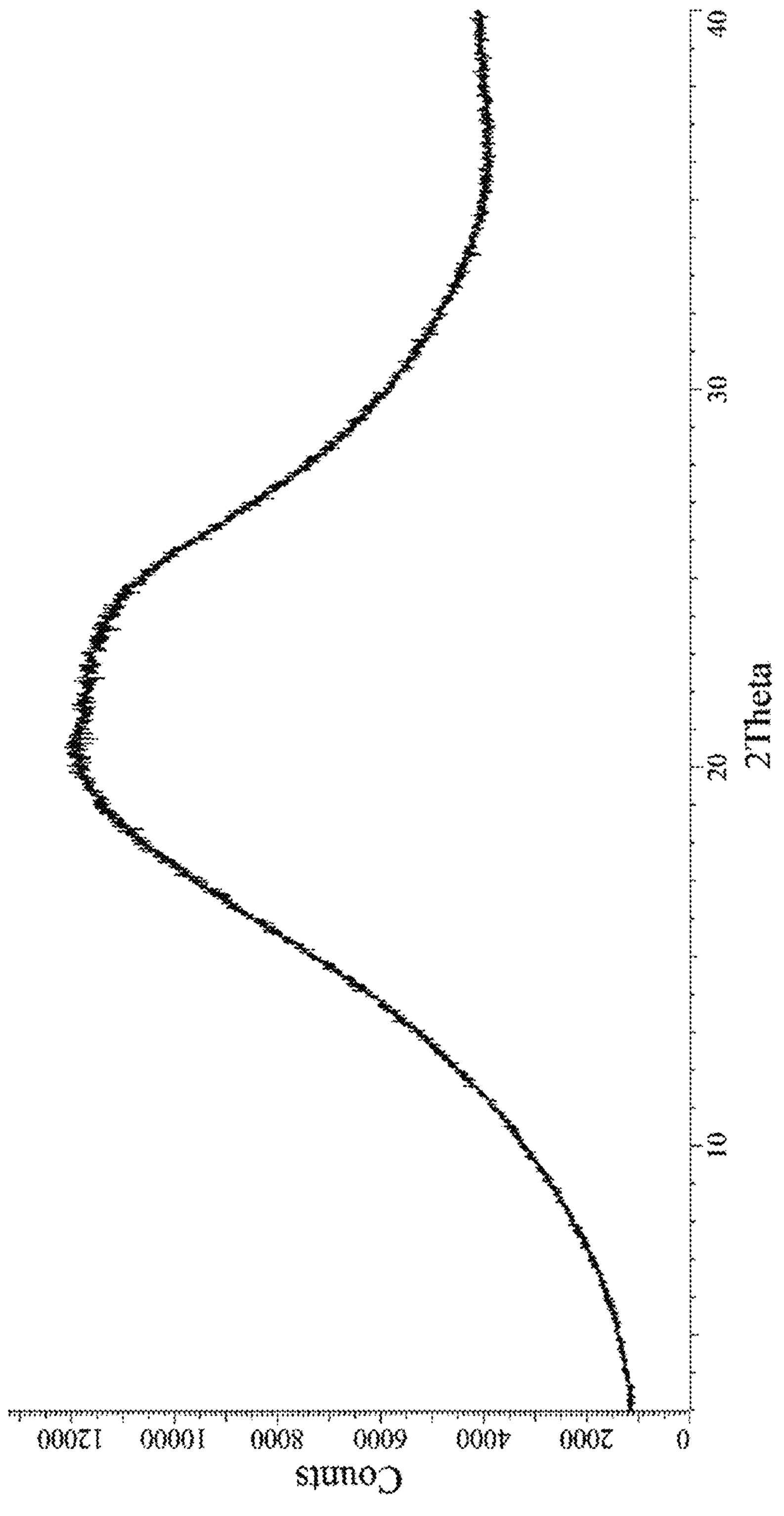
FIG. 6 shows the PXRD pattern of amorphous 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3).

In one embodiment, the invention provides an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) having:

(1) a powder X-ray diffraction (PXRD) pattern (2θ) comprising: one, two, three, four, five, or more than five peaks at 2θ values essentially the same as in FIG. 6;

(2) a Raman spectrum comprising: (a) one, two, three, four, five, or more than five wavenumber ($cm^{-1}$) values selected from the group consisting of the values in Table 6 in $cm^{-1}$±2 $cm^{-1}$; or (b) wavenumber ($cm^{-1}$) values essentially the same as in FIG. 7;

(3) a $^{13}C$ solid state NMR spectrum (ppm) comprising: (a) one, two, three, four, five, or more than five resonance (ppm) values selected from the group consisting of the values in Table 7 in ppm±0.2 ppm; or (b) resonance (ppm) values essentially the same as in FIG. 8; or (4) a $^{19}F$ solid state NMR spectrum (ppm) comprising: (a) one or two resonance (ppm) values selected from the group consisting of the values in Table 8 in ppm±0.2 ppm; or (b) resonance (ppm) values essentially the same as in FIG. 9;

or any combination of (1), (2)(a)-(b), (3)(a)-(b), and (4)(a)-(b), provided they are not inconsistent with each other.

In another aspect, the invention provides an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) having a Raman spectrum comprising wavenumber ($cm^{-1}$) values of: 1590, 1570, and 1519 $cm^{-1}$±2 $cm^{-1}$.

In another aspect, the invention provides an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a $^{13}C$ solid state NMR spectrum comprising resonance (ppm) values of: 152.4 ppm±0.5 ppm.

In one embodiment, the invention provides an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1) having a $^{13}C$ solid state NMR spectrum comprising resonance (ppm) values of: 152.4 ppm±0.5 ppm; and one or two resonance (ppm) values selected from the group consisting of: 50.2 and 41.5 ppm±0.5 ppm.

In one embodiment, the invention provides an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) having a $^{13}C$ solid state NMR spectrum comprising resonance (ppm) values of: 152.4, 50.2, and 41.5 ppm±0.5 ppm.

In another aspect, the invention provides an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) having a $^{19}F$ solid state NMR spectrum comprising resonance (ppm) values of −81.4 ppm±0.5 ppm.

In another aspect, the invention provides an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) having a $^{19}F$ solid state NMR spectrum comprising resonance (ppm) values of: −97.4 and −81.4 ppm±0.5 ppm.

In another aspect, the invention provides a pharmaceutical composition comprising an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein, and a pharmaceutically acceptable carrier or excipient.

In another aspect, the invention provides a method of treating cancer in a subject in need thereof, comprising administering to the subject a therapeutically effective amount of an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein.

In another aspect, the invention provides a method of treating cancer in a subject in need thereof, comprising administering to the subject an amount of an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein, and an amount of an additional anticancer agent, wherein the amounts of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) and the additional anticancer agent together are effective in treating cancer.

In another aspect, the invention provides a method of treating cancer in a subject in need thereof, comprising administering to the subject a therapeutically effective amount of a pharmaceutical composition comprising an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein.

In another aspect, the invention provides a method of treating cancer in a subject in need thereof, comprising administering to the subject an amount of a pharmaceutical composition comprising an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein, and an amount of an additional anticancer agent, wherein the amounts of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) and the additional anticancer agent together are effective in treating cancer.

In another aspect, the invention provides use of an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein, for the treatment of cancer.

In another aspect, the invention provides use of a pharmaceutical composition comprising an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein, for the treatment of cancer.

In yet another aspect, the invention provides use of an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3), according to the aspects or embodiments described herein, in the manufacture of a medicament for the treatment of cancer.

In each of the aspects and embodiments of amorphous described herein, the amorphous form may be a substantially pure amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3).

Each of the embodiments described herein for amorphous 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) may be combined with other such embodiments, provided the embodiments are not inconsistent with each other.

Treatment Methods and Pharmaceutical Compositions

A wide variety of cancers, including solid tumors, lymphomas and leukemias, are amenable to the methods disclosed and uses described herein. Types of cancer that may be treated include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; T-cell lymphoma, B-cell lymphoma, hairy cell lymphoma, Burkitt's lymphoma, plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; and trophoblastic tumor.

Other cancers that can be treated using the methods and uses described herein include, but not limited to, adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leiomyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; and paraganglioma nonchromaffin.

In some embodiments, cancers that can be treated using the methods and uses described herein include, but not limited to, angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; neurofibromatosis; and cervical dysplasia.

In some embodiments of the methods and uses described herein, the cancer is advanced or metastatic cancer. In some embodiments of the methods and uses described herein, the cancer is early stage or non-metastatic cancer.

In some embodiments of the methods and uses described herein, the cancer is selected from the group consisting of colon cancer, rectal cancer, colorectal cancer, bladder cancer, gastric cancer, esophageal cancer, head and neck cancer, myelodysplastic syndrome, brain cancer (including astrocytoma, meningioma, and glioblastoma, CNS cancer, and malignant glioma), hepatocellular cancers (including hepatocellular carcinoma), thyroid cancer, lung cancer (including non-small cell lung cancer (NSCLC) and small cell lung cancer (SCLC)), acute and chronic leukemia, B-cell lymphoma, Waldenström's macroglobulinemia, T-cell lymphoma, hairy cell lymphoma, diffuse large B cell lymphoma, Hodgkin's lymphoma, non-Hodgkin's lymphoma, Burkitt lymphoma, pancreatic cancer (including pancreatic carcinoma), melanoma, multiple myeloma, renal cancer (including renal cell carcinoma), cervical cancer, urothelial cancer, prostate cancer (including castration-resistant prostate cancer), ovarian cancer, breast cancer (including triple-negative breast cancer, triple-positive breast cancer, estrogen receptor-positive breast cancer, hormone receptor-positive breast cancer, and hormone receptor-negative breast cancer).

In some embodiments, the cancer is selected from the group consisting of colon cancer, gastric cancer, thyroid cancer, lung cancer, leukemia, B-cell lymphoma, T-cell lymphoma, hairy cell lymphoma, Hodgkin's lymphoma, non-Hodgkin's lymphoma, Burkitt's lymphoma, pancreatic cancer, melanoma, brain cancer, CNS cancer, renal cancer, prostate cancer, ovarian cancer, and breast cancer.

In some embodiments of the methods and uses described herein, the breast cancer is BRCA1- or BRCA2-mutated breast cancer.

In some embodiments of the methods and uses described herein, the breast cancer is PIK3CA-mutated cancer breast cancer.

In some embodiments of the methods and uses described herein, the breast cancer is refractory or resistant to treatment with, or has progressed on, one or more standard of care agents. In some such embodiments, the breast cancer is refractory or resistant to treatment with, or has progressed on, an antiestrogen, such as an aromatase inhibitor, a SERD (Selective Estrogen Receptor Degrader), or a SERM (Selective Estrogen Receptor Modulator).

In some embodiments of each of the methods and uses described herein, the breast cancer is hormone receptor (HR)-positive (HR+) breast cancer, i.e., the breast cancer is estrogen receptor (ER)-positive (ER+) and/or progesterone receptor (PR)-positive (PR+).

In some embodiments, the breast cancer is hormone receptor (HR)-negative (HR), i.e., the breast cancer is estrogen receptor (ER)-negative (ER−) and progesterone receptor (PR)-negative (PR−).

In some embodiments, the breast cancer is human epidermal growth factor receptor 2 (HER2)-positive (HER2+).

In some embodiments, the breast cancer is human epidermal growth factor receptor 2 (HER2)-negative (HER2−). In some such embodiments, the breast cancer is is estrogen receptor alpha (ERα)-negative.

In some embodiments, the breast cancer is triple negative breast cancer (TNBC), i.e., the breast cancer is ER−, PR− and HER2−.

In some embodiments, the breast cancer is selected from the group consisting of HR+/HER2− breast cancer, HR+/HER2+ breast cancer, HR−/HER2+ breast cancer, and triple negative breast cancer (TNBC). In some such embodiments, the breast cancer is androgen-dependent or AR+ breast cancer. In some such embodiments, the breast cancer is BRCA1- or BRCA2-mutated breast cancer.

In some embodiments, the methods and uses of the present invention may further comprise one or more additional anti-cancer agents. In some embodiments, the additional anti-cancer agent is a chemotherapeutic agent or an inhibitor of an immunosuppression component.

In some embodiments, a chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents, antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab, antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors, cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

An inhibitor of an immunosuppression component can be an inhibitor of an immune checkpoint molecule or gene, a metabolic enzyme, an immunosuppressive cytokine, $T_{reg}$ cells, or any combination thereof. As used herein, the term "immunosuppression component" refers to one or more cells, proteins, molecules, compounds or complexes providing inhibitory signals to assist in controlling or suppressing an immune response. For example, immunosuppression components include those molecules that partially or totally block immune stimulation; decrease, prevent or delay immune activation; or increase, activate, or up regulate immune suppression. "Controlling or suppressing an immune response," as used herein, means reducing any one or more of antigen presentation, T cell activation, T cell proliferation, T cell effector function, cytokine secretion or production, and target cell lysis. Such modulation, control or suppression can promote or permit the persistence of a hyperproliferative disease or disorder (e.g., cancer, chronic infections).

Immune checkpoint molecules include immune checkpoint ligands such as, PD-L1, PD-L2, CD80, CD86, B7-H3, B7-H4, HVEM, adenosine, GAL9, VISTA, CEACAM-1, CEACAM-3, CEACAM-5, PVRL2, and immune checkpoint receptors such as, PD-1, CTLA-4, BTLA, KIR, LAG3, TIM3, A2aR, CD244/2B4, CD160, TIGIT, LAIR-1, and PVRIG/CD112R). Metabolic enzymes include arginase and indoleamine 2,3-dioxygenase (IDO)), and immunosuppressive cytokines include IL-10, IL-4, IL-1 RA, and IL-35. In certain embodiments, an inhibitor of immunosuppression component is a small molecule, an antisense molecule, a ribozyme, an RNAi molecule (e.g., siRNA), an antibody or antigen binding fragment thereof, or fusion polypeptide (e.g., Fc fusion protein).

An antibody specific for PD-1 may be pidilizumab, nivolumab, pembrolizumab, MEDI0680 (formerly AMP-514), AMP-224, sasanlimab (PF-06801591), or BMS-936558.

An antibody specific for PD-L1 may be MDX-1105 (BMS-936559), durvalumab (formerly MED14736), atezolizumab (formerly MPDL3280A), or avelumab (formerly MSB0010718C). A compound specific for PD-L1 may be BMS-1001, or BMS-1166.

A CTLA4 inhibitor may be a CTLA4 specific antibody, such as tremelimumab or ipilimumab, or a CTLA4-Ig fusion protein (e.g., abatacept, belatacept).

A LAG3 inhibitor may be LAG525, IMP321, IMP701, 9H12, or BMS-986016.

An IDO inhibitor may be levo-1-methyl tryptophan, epacadostat (INCB024360; Liu et al., *Blood* 115:3520-30, 2010), ebselen (Terentis et al., *Biochem.* 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In some embodiments of each of the methods and uses described herein, the patient or subject is an adult human. In some embodiments, the subject is a woman of any menopausal status or a man. In some embodiments, the subject is a post-menopausal woman or a man. In some embodiments, the subject is a post-menopausal woman. In some embodiments, the subject is a pre-menopausal or peri-menopausal woman. In some embodiments, the subject is a pre-menopausal or peri-menopausal woman treated with a luteinizing hormone-releasing hormone (LHRH) agonist. In some such embodiments, the subject is a man. In some embodiments, the subject is a man treated with an LHRH or gonadotropin-releasing hormone (GnRH) agonist.

In some embodiments of each of the methods and uses described herein, the invention relates to neoadjuvant therapy, adjuvant therapy, first-line therapy, second-line therapy, second-line or later lines of therapy, or third-line or later lines of therapy. In each case as further described herein, the cancer may be localized, advanced or metastatic, and the intervention may occur at point along the disease continuum (i.e., at any stage of the cancer).

The treatment regimen for a compound of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi2-test the U-test according to Mann and Whitney, the Kruskal-Wallis test (H-test), Jonckheere-Terpstrattesty and the Wilcon on-test.

The efficacy of the methods and uses described herein in certain tumors may be enhanced by combination with other approved or experimental cancer therapies, e.g., radiation, surgery, chemotherapeutic agents, targeted therapies, agents that inhibit other signaling pathways that are dysregulated in tumors, and other immune enhancing agents, such as PD-1 or PD-L1 antagonists and the like. The methods and uses of the current invention may further comprise one or more additional anti-cancer agents.

Administration of crystalline or amorphous forms of the invention may be affected by any method that enables delivery of the compound to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, the crystalline or amorphous form of the present invention may be administered as a single bolus, as several divided doses administered over time, or the dose may be proportionally reduced or increased as indicated by the exigencies of the therapeutic situation. It may be particularly advantageous to formulate a therapeutic agent in a dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention may be dictated by and directly dependent on (a) the unique characteristics of the solid form and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose may be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present invention.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compounds or pharmaceutical compositions, taking into consideration factors such as the severity of the disorder or condition, the rate of administration, the disposition of the compound and the discretion of the prescribing physician. The dosage ranges set forth herein are exemplary only and are not intended to limit the scope or practice of the claimed solid form or pharmaceutical composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein The dosage of the crystalline or amorphous form of the invention is in the range from about 1 to 2000 mg/day, from about 10 to about 1000 mg/day, from about 10 to about 500 mg/day, from about 10 to about 250 mg/day, from about 10 to about 100 mg/day, or from about 10 to about 50 mg/day. The therapeutically effective dosages may be administered in one or multiple doses.

A "pharmaceutical composition" refers to a mixture of one or more of the therapeutic agents described herein, or a pharmaceutically acceptable salt, solvate, hydrate or prodrug thereof as an active ingredient, and at least one pharmaceutically acceptable carrier or excipient. In some embodiments, the pharmaceutical composition comprises two or more pharmaceutically acceptable carriers and/or excipients.

As used herein, a "pharmaceutically acceptable carrier" refers to a carrier or diluent that does not cause significant irritation to an organism and does not abrogate the biological activity and properties of the active compound or therapeutic agent.

The pharmaceutical acceptable carrier may comprise any conventional pharmaceutical carrier or excipient. The choice of carrier and/or excipient will to a large extent depend on factors such as the particular mode of administration, the effect of the excipient on solubility and stability, and the nature of the dosage form.

In one embodiment, the invention relates to a pharmaceutical composition comprising crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1), and a pharmaceutically acceptable carrier or excipient.

In one embodiment, this invention relates to a pharmaceutical composition comprising amorphous 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3) and a pharmaceutically acceptable carrier or excipient.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus, for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid pharmaceutical compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Pharmaceutical compositions of the present invention may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Methods of preparing various pharmaceutical compositions with a specific amount of active compound are known, or will be apparent, to those skilled in this art. For examples, see Remington's Pharmaceutical Sciences, Mack Publishing Company, Easter, Pa., 19th Edition (1995).

The crystalline and amorphous forms of the invention may be administered orally. Oral administration may involve swallowing, so that the therapeutic agent enters the gastrointestinal tract, or buccal or sublingual administration may be employed by which the therapeutic agent enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The crystalline and amorphous forms of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, the crystalline or amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide may make up from 1 wt % to 80 wt % of the dosage form, more typically from 5 wt % to 60 wt % of the dosage form. In addition to the active agent, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant may comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets may contain from about 1 wt % to about 80 wt % active agent, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Capsules (made, for example, from gelatin or HPMC), blisters and cartridges for use in an inhaler or insufflator may be formulated to contain a powder mix of the therapeutic agent, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles may be found in Verma et al, Current Status of Drug Delivery Technologies and Future Directions, Pharmaceutical Technology On-line, (2001) 25:1-14. The use of chewing gum to achieve controlled release is described in WO 00/35298. The disclosures of these references are incorporated herein by reference in their entireties.

The crystalline and amorphous forms of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of therapeutic agents used in the preparation of parenteral solutions may potentially be increased by the use of appropriate formulation techniques, such as the incorporation of solubility-enhancing agents.

The crystalline and amorphous forms of the invention may be in the form of a kit suitable for administration of the pharmaceutical composition. Such kits may comprise the active agent in the form of a pharmaceutical composition, which pharmaceutical composition comprises an active agent, or a pharmaceutically acceptable salt or solvate thereof, and a pharmaceutically acceptable carrier. The kit may contain means for separately retaining the pharmaceutical composition, such as a container, divided bottle, or divided foil packet. An example of such a kit is the familiar blister pack used for the packaging of tablets, capsules and the like. To assist in compliance, the kit typically includes directions for administration and may be provided with a memory aid. The kit may further comprise other materials that may be useful in administering the medicament, such as diluents, filters, IV bags and lines, needles and syringes, and the like.

Numbered Embodiments

Embodiment 1 is a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate, having a powder X-ray diffraction (PXRD) pattern comprising peaks at 2θ values of: 7.8, 6.4, and 5.2° 2θ±0.2°2θ.

Embodiment 2 is the crystalline form of embodiment 1, having a PXRD pattern further comprising a peak at a 2θ value of: 17.2°2θ±0.2°2θ.

Embodiment 3 is the crystalline form of embodiment 1 or embodiment 2, having a Raman spectrum comprising wavenumber ($cm^{-1}$) values of: 1694 and 1680 $cm^{-1\pm2}$ $cm^{-1}$.

Embodiment 4 is the crystalline form of any one of embodiments 1 to 3, having a $^{13}C$ solid state NMR spectrum comprising resonance (ppm) values of: 47.3, 125.4, and 153.6 ppm±0.2 ppm.

Embodiment 5 is the crystalline form of any one of embodiments 1 to 4, having a $^{19}F$ solid state NMR spectrum comprising resonance (ppm) values of: −93.2 and −80.4 ppm±0.2 ppm.

Embodiment 6 is a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate, having a Raman spectrum comprising wavenumber ($cm^{-1}$) values of: 1694 and 1680 $cm^{-1}$±2 $cm^{-1}$.

Embodiment 7 is a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate, having a $^{13}C$ solid state NMR spectrum comprising resonance (ppm) values of: 47.3, 125.4, and 153.6 ppm±0.2 ppm.

Embodiment 8 is a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate, having a $^{19}F$ solid state NMR spectrum comprising resonance (ppm) values of: −93.2 and −80.4 ppm±0.2 ppm.

Embodiment 9 is a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate, having: (a) a powder X-ray diffraction (PXRD) pattern comprising peaks at 2θ values of: 7.8, 6.4, and 5.2°2θ±0.2°2θ; (b) a Raman spectrum comprising wavenumber ($cm^{-1}$) values of: 1694 and 1680 $cm^{-1}$+2 $cm^{-1}$; (c) a $^{13}C$ solid state NMR spectrum comprising resonance (ppm) values of: 47.3, 125.4, and 153.6 ppm±0.2 ppm; or (d) a $^{19}F$ solid state NMR spectrum comprising resonance (ppm) values of: −93.2 and −80.4 ppm±0.2 ppm; or any combination of (a), (b), (c) and (d).

Embodiment 10 is a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate, having: (a) a powder X-ray diffraction (PXRD) pattern comprising peaks at 2θ values of: 7.8, 6.4, 5.2, and 17.2° 2θ±0.2°2θ; (b) a Raman spectrum comprising wavenumber ($cm^{-1}$) values of: 1694 and 1680 $cm^{-1}$±2 $cm^{-1}$; (c) a $^{13}C$ solid state NMR spectrum comprising resonance (ppm) values of: 47.3, 125.4, and 153.6 ppm±0.2 ppm; or (d) a $^{19}F$ solid state NMR spectrum comprising resonance (ppm) values of: −93.2 and −80.4 ppm±0.2 ppm; or any combination of (a), (b), (c) and (d).

Embodiment 11 is the crystalline form of any one of embodiments 1 to 10, wherein the crystalline form is substantially pure.

Embodiment 12 is the crystalline form of any one of embodiments 1 to 11, wherein the crystalline form is 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 1).

Embodiment 13 is a crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno

Figure 5:
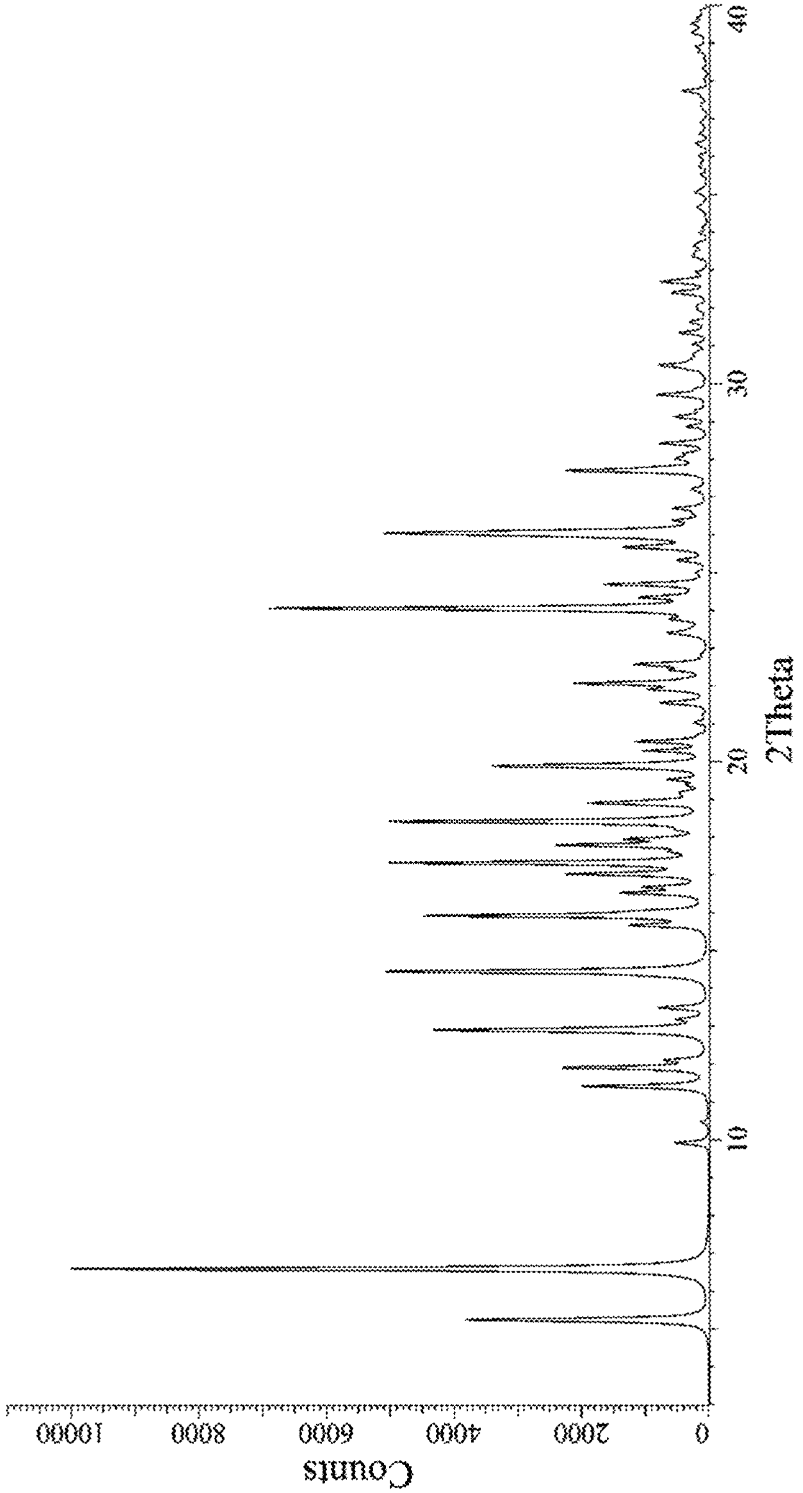
FIG. 5 shows the PXRD pattern of crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide hydrate (Form 2).

[3,2-b]pyridine-3-carboxamide hydrate, having a powder X-ray diffraction (PXRD) pattern essentially the same as FIG. 5.

Embodiment 14 is the crystalline form of embodiment 13, having the PXRD peak list essentially the same as Table 5.

Embodiment 15 is the crystalline form of any one of embodiments 1-2, 9-10, or 13-14, wherein the PXRD peaks were collected using CuK$\overline{\alpha}$ radiation at 1.5418λ.

Embodiment 16 is a pharmaceutical composition comprising the crystalline form of any one of embodiments 1 to 15, and a pharmaceutically acceptable carrier or excipient.

Embodiment 17 is a method of treating cancer in a subject comprising administering to the subject in need thereof, a therapeutically effective amount of the crystalline form of any one of embodiments 1 to 15.

Embodiment 18 is the method of embodiment 17, wherein the cancer is selected from the group consisting of colon cancer, gastric cancer, thyroid cancer, lung cancer, leukemia, B-cell lymphoma, T-cell lymphoma, hairy cell lymphoma, Hodgkin's lymphoma, non-Hodgkin's lymphoma, Burkitt's lymphoma, pancreatic cancer, melanoma, brain cancer, CNS cancer, renal cancer, prostate cancer, ovarian cancer, and breast cancer.

Embodiment 19 is an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide.

Embodiment 20 is the amorphous form of embodiment 19, having a powder X-ray diffraction (PXRD) pattern essentially the same as FIG. 6.

Embodiment 21 is the amorphous form of embodiment 19 or embodiment 20, having a Raman spectrum comprising wavenumber ($cm^{-1}$) values of: 1590, 1570, and 1519 $cm^{-1}$±2 $cm^{-1}$.

Embodiment 22 is the amorphous form of any one of embodiments 19-21, having a $^{13}C$ solid state NMR spectrum comprising resonance (ppm) values of: 152.4, 50.2, and 41.5 ppm±0.5 ppm.

Embodiment 23 is the amorphous form of any one of embodiments 19-22, having a $^{19}F$ solid state NMR spectrum comprising a resonance (ppm) value of: −97.4 and −81.4 ppm±0.5 ppm.

Embodiment 24 is an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide, having a Raman spectrum comprising wavenumber ($cm^{-1}$) values of: 1590, 1570, and 1519 $cm^{-1}$±2 $cm^{-1}$.

Embodiment 25 is an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide, having a $^{13}C$ solid state NMR spectrum comprising resonance (ppm) values of: 152.4, 50.2, and 41.5 ppm±0.5 ppm.

Embodiment 26 is an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide, having a $^{19}F$ solid state NMR spectrum comprising resonance (ppm) values of: −97.4 and −81.4 ppm±0.5 ppm.

Embodiment 27 is an amorphous form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide, having: (a) a powder X-ray diffraction (PXRD) pattern essentially the same as FIG. 6; (b) a Raman spectrum comprising wavenumber ($cm^{-1}$) values of: 1590, 1570, and 1519 $cm^{-1}$±2 $cm^{-1}$; (c) a $^{13}C$ solid state NMR spectrum comprising resonance (ppm) values of: 152.4, 50.2, and 41.5 ppm±0.5 ppm; or (d) a $^{19}F$ solid state NMR spectrum comprising resonance (ppm) values of: −97.4 and −81.4 ppm±0.5 ppm; or any combination of (a), (b), (c) and (d).

Embodiment 28 is a pharmaceutical composition comprising the amorphous form of any one of embodiments 19 to 27, and a pharmaceutically acceptable carrier or excipient.

Embodiment 29 is a method of treating cancer in a subject in need thereof, comprising administering to the subject a therapeutically effective amount of the amorphous form of any one of embodiments 19 to 27.

Embodiment 30 is the method of embodiment 29, wherein the cancer is selected from the group consisting of colon cancer, gastric cancer, thyroid cancer, lung cancer, leukemia, B-cell lymphoma, T-cell lymphoma, hairy cell lymphoma, Hodgkin's lymphoma, non-Hodgkin's lymphoma, Burkitt's lymphoma, pancreatic cancer, melanoma, brain cancer, CNS cancer, renal cancer, prostate cancer, ovarian cancer, and breast cancer.

Embodiment 31 is the method of any one of embodiments 17-18 or 29-30, further comprising administering another anti-cancer agent.

EXAMPLES

The examples and preparations provided below further illustrate and exemplify aspects and embodiments of the invention. It is to be understood that the scope of the present invention is not limited by the scope of the following examples.

General Instrumentation Method (a) Powder X-Ray Diffraction

Powder X-ray diffraction analysis was conducted using a Bruker AXS D8 Endeavor diffractometer equipped with a Cu radiation source. The divergence slit was set at 15 mm continuous illumination. Diffracted radiation was detected by a PSD-Lynx Eye detector, with the detector PSD opening set at 2.99 degrees. The X-ray tube voltage and amperage were set to 40 kV and 40 mA respectively. Data was collected at the Cu wavelength ($CuK_{\overline{\alpha}}$=1.5418 λ) in the Theta-Theta goniometer from 3.0 to 40.0 degrees 2-Theta using a step size of 0.01 degrees and a step time of 1.0 second. The antiscatter screen was set to a fixed distance of 1.5 mm. Samples were rotated during data collection. Samples were prepared by placing them in a silicon low background sample holder and rotated during collection. Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of 5% were generally chosen. Typically, the peaks which were not resolved or were consistent with noise were not selected. A typical error associated with the peak position from PXRD stated in USP up to +/−0.2° 2-Theta (USP-941).

(b) ssNMR Spectroscopy

Solid state NMR (ssNMR) analysis was conducted on a CPMAS probe positioned into a Bruker-BioSpin Avance III 500 MHz ($^{1}H$ frequency) NMR spectrometer. A magic angle spinning rate of 15.0 kHz was used.

$^{13}C$ ssNMR spectra were collected using a proton decoupled cross-polarization magic angle spinning (CP-MAS) experiment. A phase modulated proton decoupling field of 80-100 kHz was applied during spectral acquisition. The cross-polarization contact time was set to 2 ms. Spectra were collected with a recycle delay of 17 seconds, and 3.15 seconds for Form 1 and Form 3 of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide. The number of scans was adjusted to obtain an adequate signal to noise ratio. The $^{13}C$ chemical shift scale was referenced using an $^{13}C$ CPMAS experiment on an external standard of crystalline adamantane, setting its up-field resonance to 29.5 ppm (as determined from neat TMS).

$^{19}F$ ssNMR spectra were collected using a proton decoupled magic angle spinning (MAS) experiment. A phase modulated proton decoupling field of 80-100 kHz was applied during spectral acquisition. Spectra were collected with a recycle delay of 45 seconds, and 3 seconds for 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide Form 1 and 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide Form 3 respectively. The number of scans was adjusted to obtain an adequate signal to noise ratio. The $^{19}F$ chemical shift scale was referenced using an $^{19}F$ MAS experiment on an external standard of trifluoroacetic acid (50%/50% v/v in $H_2O$), setting its resonance to −76.54 ppm.

Automatic peak picking was performed using Bruker-BioSpin TopSpin version 3.6 software. Generally, a threshold value of 2% relative intensity was used for preliminary peak selection. The output of the automated peak picking was visually checked to ensure validity and adjustments were manually made, if necessary. Although specific solid state NMR peak values were reported herein there does exist a range for these peak values due to differences in instruments, samples, and sample preparation. This is common practice in the art of solid state NMR because of the variation inherent in peak positions. A typical variability for $^{13}C$ chemical shift x-axis value is on the order of plus or minus 0.2 ppm for a crystalline solid and plus or minus 0.5 ppm for an amorphous solid. The solid state NMR peak heights reported herein are relative intensities. Solid state NMR intensities can vary depending on the actual setup of the experimental parameters and the thermal history of the sample.

(c) FT-Raman Spectroscopy

Raman spectra were collected using a Thermo Scientific iS50 FT-Raman accessory attached to a FT-IR instrument. The spectrometer is equipped with a $CaF_2$ beamsplitter, a 1064 nm diode laser and a room temperature InGaAs detector. Prior to data acquisition, a calibration verification was conducted using a polystyrene reference.

Powder samples were prepared in glass NMR tubes, and spectra in the range 3700-100 $cm^{-1}$ were acquired at 2 $cm^{-1}$ resolution using a laser power of 300 mW. The number of scans was adjusted to ensure good signal-to-noise and a Happ-Genzel apodisation function was applied to minimise spectral aberrations.

Spectra were normalized by setting the intensity of the most intense peak. Peaks were then identified using the automatic peak picking function in the OPUS v8.2 software (Bruker Optik GmbH) with the sensitivity set to 4% for 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide Form 1 crystalline free form non-stoichiometric [0.5-1]hydrate and 2% for 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide Form 3 amorphous free form. Peak positions and relative peak intensities were extracted and tabulated. The variability in the peak positions with this experimental configuration is within ±2 $cm^{-1}$.

Since FT-Raman and dispersive Raman are similar techniques, peak positions disclosed herein for FT-Raman spectra are consistent with those which are observed using a dispersive Raman measurement, provided that instrument is calibrated appropriately.

Example 1

Preparation and characterization of crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide free form hydrate (Form 1)

7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (952.3 mg, 1.20 mmol) was combined with acetonitrile (13.0 mL) and 1 N NaOH (0.6 mL, 0.6 mmol) in a 40 mL vial with a stirbar. The mixture was heated to reflux. During this time, most solids dissolved but not all. The mixture was a hazy, pale orange color. The mixture was filtered using pre-warmed glass funnel and filter paper. The resulting filtrate was pale orange with no apparent undissolved solids. Hot water (4 mL, ~90° C.) was added in 1 mL increments to produce a yellow precipitate. The mixture was allowed to cool to room temperature. After stirring at room temperature overnight, the yellow solid was collected and washed with 4:1 Acetonitrile/water (2×2.00 mL). After removing a small amount of solid for analysis with PXRD & Raman spectroscopy, the remaining solid was dried on the filter frit for approximately 2 hours. 512.4 mg, 54%. Crystals suitable for single crystal X-ray diffraction were grown by slow evaporation of a saturated solution of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide in acetonitrile.

The PXRD pattern of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide Form 1 crystalline free from is provided in FIG. 1. The PXRD peak list is further provided in Table 1.

TABLE 1

| PXRD peak list of Form 1, crystalline free form hydrate. | |
|---|---|
| Angle (° 2-Theta) | Rel. Intensity |
| 5.2 | 11.5 |
| 6.4 | 11.7 |
| 7.8 | 55.6 |
| 9.6 | 9.7 |
| 12.9 | 8.7 |
| NA | NA |
| NA | NA |
| 14.1 | 30.1 |
| 14.8 | 12.8 |
| 15.4 | 16.4 |
| 15.9 | 10.0 |
| 16.2 | 12.0 |
| 17.2 | 100 |
| NA | NA |
| 18.8 | 16.6 |
| NA | NA |
| 20.1 | 66.4 |
| 21.4 | 16.0 |
| 21.9 | 40.6 |
| NA | NA |
| 23.0 | 65.1 |
| 23.2 | 59.0 |
| 23.5 | 88.4 |
| 24.8 | 80.2 |
| NA | NA |
| 25.6 | 18.5 |
| NA | NA |
| NA | NA |
| 26.7 | 45.8 |
| 28.0 | 18.2 |
| NA | NA |
| 28.8 | 15.9 |
| 29.2 | 26.5 |
| NA | NA |
| NA | NA |
| 31.4 | 20.4 |
| 33.9 | 7 |
| NA | NA |
| NA | NA |

Table 2 shows the peak list extracted from the Raman spectrum collected from 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide Form 1 crystalline free form non-stoichiometric [0.5-1]hydrate. See also the Raman spectrum of the same form in FIG. 2.

TABLE 2

| Wavenumber ($cm^{-1}$) | Relative Intensity (%) |
|---|---|
| 266 | 17 |
| 286 | 16 |
| 297 | 24 |
| 329 | 14 |
| 351 | 17 |
| 419 | 20 |
| 443 | 25 |
| 477 | 16 |
| 500 | 37 |
| 516 | 22 |
| 532 | 18 |
| 543 | 24 |
| 572 | 14 |
| 604 | 39 |
| 628 | 12 |
| 651 | 23 |
| 671 | 16 |
| 716 | 11 |
| 749 | 20 |
| 796 | 12 |
| 834 | 10 |
| 896 | 11 |
| 980 | 13 |
| 1032 | 15 |
| 1057 | 23 |
| 1099 | 17 |
| 1145 | 21 |
| 1158 | 28 |
| 1190 | 14 |
| 1214 | 18 |
| 1291 | 50 |
| 1331 | 27 |
| 1372 | 42 |
| 1384 | 28 |
| 1404 | 27 |
| 1433 | 33 |
| 1478 | 22 |
| 1514 | 23 |
| 1539 | 38 |
| 1565 | 59 |
| 1595 | 100 |
| 1680 | 16 |
| 1694 | 20 |
| 2213 | 96 |
| 2239 | 35 |
| 2938 | 60 |
| 2946 | 45 |
| 2974 | 27 |
| 2985 | 22 |
| 3013 | 17 |
| 3068 | 18 |
| 3101 | 12 |

Table 3 shows the $^{13}C$ solid state NMR peak list for 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide Form 1 crystalline free form non-stoichiometric [0.5-1]hydrate. See also the $^{13}C$ solid state NMR spectrum for the same form in FIG. 3.

TABLE 3

| $^{13}C$ Chemical Shift (ppm) | Relative Intensity (%) |
|---|---|
| 164.2 | 28 |
| 158.1 | 46 |
| 157.7 | 41 |
| 153.6 | 100 |
| 150.6 | 33 |
| 146.7 | 47 |
| 145.0 | 44 |
| 143.4 | 51 |
| 142.2 | 49 |
| 135.7 | 83 |
| 134.7 | 56 |
| 132.4 | 14 |
| 131.1 | 57 |
| 128.5 | 46 |
| 128.1 | 37 |
| 125.4 | 50 |
| 121.4 | 15 |
| 119.6 | 92 |
| 118.2 | 22 |
| 117.1 | 20 |
| 90.0 | 63 |
| 82.1 | 53 |
| 56.6 | 76 |
| 50.2 | 74 |
| 49.6 | 83 |

TABLE 3-continued

| $^{13}C$ Chemical Shift (ppm) | Relative Intensity (%) |
|---|---|
| 47.3 | 64 |
| 42.8 | 98 |
| 40.9 | 48 |
| 38.3 | 49 |
| 36.0 | 80 |
| 33.3 | 70 |
| 30.3 | 68 |
| 26.4 | 69 |
| 23.0 | 99 |

Table 4 shows the $^{19}F$ solid state NMR peak list for 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide Form 1 crystalline free form non-stoichiometric [0.5-1]hydrate. See also the $^{13}F$ solid state NMR spectrum for the same form in FIG. 4.

TABLE 4

| $^{19}F$ Chemical Shift (ppm) | Relative Intensity (%) |
|---|---|
| −80.4 | 84 |
| −93.2 | 100 |

Example 2

Preparation and characterization of crystalline 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide free form hydrate (Form 2)

7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide was combined with methanol (~1 mL). The mixture was allowed to sit at 50° C. for approximately 1 week. During this time crystals of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide Form 2 formed. The sample was characterized with single crystal X-ray diffraction, shown in FIG. 5. Table 5 also shows the peak list obtained from the calculated powder pattern of the same form.

TABLE 5

| Angle (degrees 2-Theta) | Rel. Int. (%) |
|---|---|
| 5.2 | 38.0 |
| 6.6 | 100.0 |
| 9.9 | 5.3 |
| 11.4 | 19.7 |
| 11.9 | 22.8 |
| 12.9 | 43.1 |
| 13.5 | 6.3 |
| 14.4 | 50.9 |
| 15.9 | 43.8 |

TABLE 5-continued

| Angle (degrees 2-Theta) | Rel. Int. (%) |
|---|---|
| 16.7 | 9.3 |
| 17.3 | 49.4 |
| 17.8 | 22.8 |
| 18.4 | 49.2 |
| 18.9 | 17.2 |
| 19.9 | 33.3 |
| 20.5 | 10.8 |
| 21.6 | 7.0 |
| 22.1 | 20.7 |
| 23.4 | 5.9 |
| 24.1 | 68.4 |
| 26.0 | 50.6 |
| 27.8 | 11.4 |
| 28.4 | 7.2 |
| 29.7 | 7.6 |
| 32.4 | 5.3 |
| 32.7 | 7.0 |

Example 3

Preparation and characterization of amorphous 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide free form (Form 3)

Figure 7:
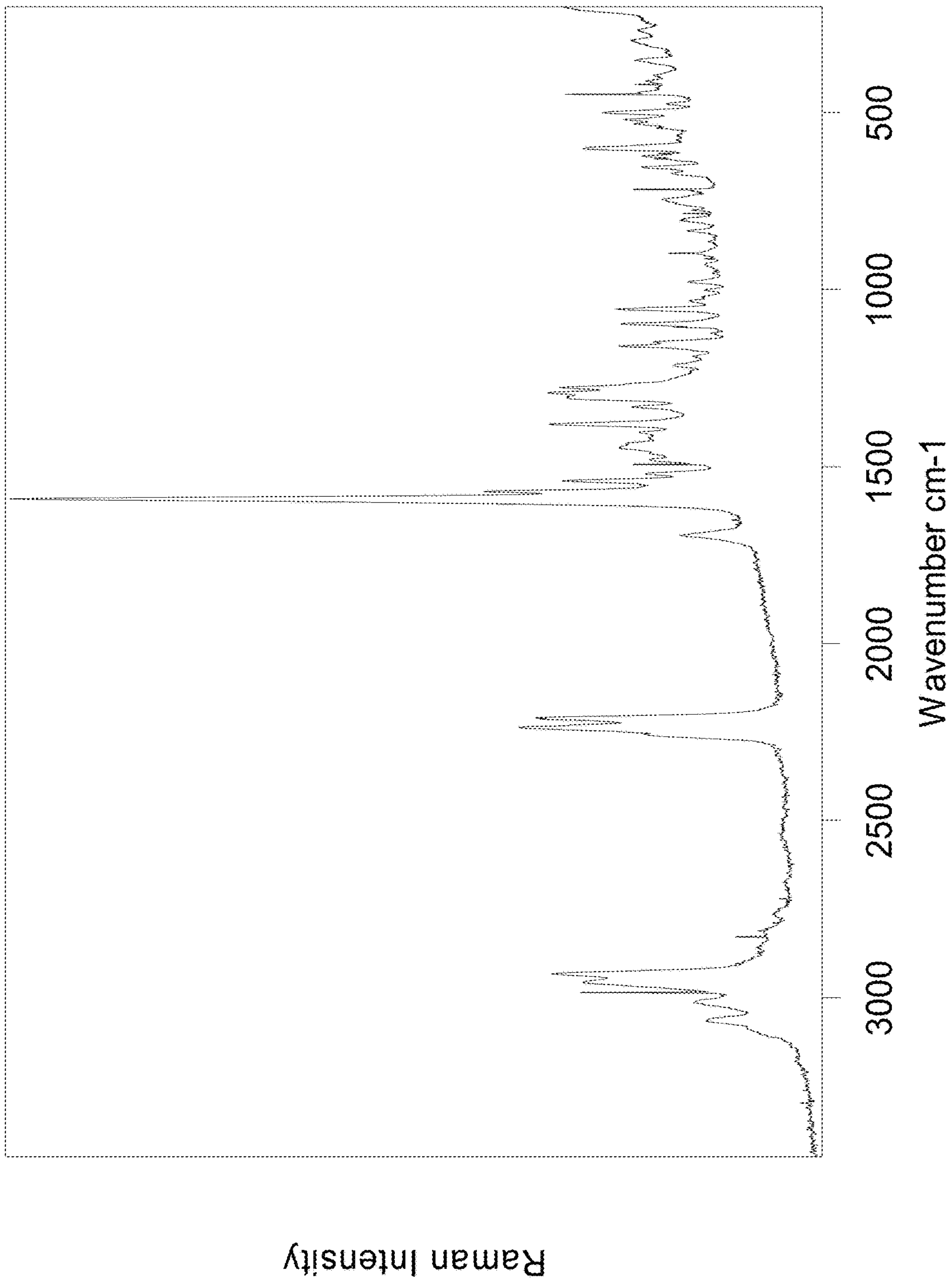
FIG. 7 shows the FT-Raman spectrum of amorphous 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3).

7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (~400 mg) and acetonitrile (30 mL) were combined in a 250 mL round bottom flask. After sonicating the mixture for 5 minutes, water (5 mL) was added and the mixture sonicated again for 5 minutes. The mixture was filtered (0.20 μm, PTFE filter) before being placed on a Labcono FreezeZone −105° C. freeze dryer. The mixture remained on the freeze dryer until all solvent was removed. FIG. 6 and FIG. 7 show the PXRD pattern and Raman spectrum, respectively, of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide Form 3 amorphous free form. Further, Table 6 is the peak list extracted from the Raman spectrum collected from the same form.

TABLE 6

| Wavenumber ($cm^{-1}$) | Relative Intensity (%) |
|---|---|
| 266 | 22 |
| 297 | 23 |
| 352 | 23 |
| 411 | 21 |
| 420 | 23 |
| 448 | 31 |
| 476 | 19 |
| 501 | 27 |
| 519 | 24 |
| 601 | 29 |
| 622 | 22 |
| 653 | 22 |
| 716 | 23 |
| 744 | 19 |
| 784 | 17 |
| 804 | 17 |
| 834 | 16 |

TABLE 6-continued

| Wavenumber ($cm^{-1}$) | Relative Intensity (%) |
|---|---|
| 896 | 18 |
| 979 | 16 |
| 1032 | 16 |
| 1056 | 25 |
| 1097 | 24 |
| 1160 | 25 |
| 1214 | 18 |
| 1277 | 32 |
| 1291 | 33 |
| 1331 | 23 |
| 1380 | 33 |
| 1448 | 25 |
| 1479 | 21 |
| 1493 | 23 |
| 1519 | 21 |
| 1540 | 32 |
| 1570 | 41 |
| 1590 | 100 |
| 1694 | 17 |
| 2209 | 35 |
| 2237 | 37 |
| 2828 | 10 |
| 2933 | 33 |
| 2956 | 29 |
| 2985 | 29 |
| 3014 | 15 |
| 3067 | 14 |

Figure 8:
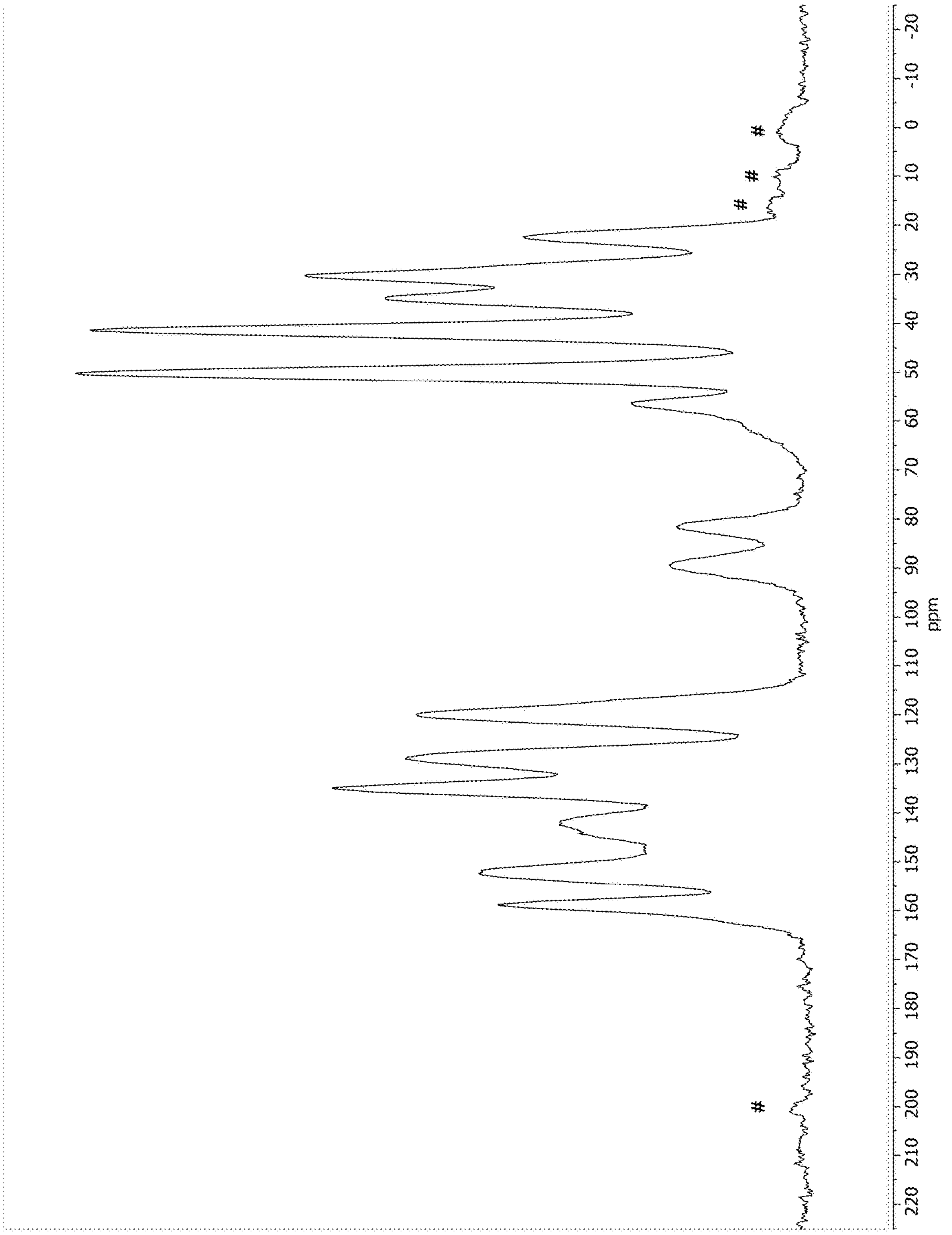
FIG. 8 shows $^{13}C$ solid state NMR spectrum of amorphous 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3).

FIG. 8 further shows the $^{13}C$ solid state NMR spectrum of 7-(5-chloro-2-(3-(5-cyano-6-((1-(3,3-difluorocyclobutyl)piperidin-4-yl)(methyl)amino)-2-methyl-4-oxopyrido[3,4-d] pyrimidin-3(4H)-yl)prop-1-yn-1-yl)phenyl)-N-(methylsulfonyl)thieno[3,2-b]pyridine-3-carboxamide Form 3 amorphous, and Table 7 shows the $^{13}C$ solid state NMR peak list of the same form.

TABLE 7

| $^{13}C$ Chemical Shift (ppm) | Relative Intensity (%) |
|---|---|
| 158.8 | 42 |
| 152.4 | 44 |
| 151.9 | 44 |
| 144.2 | 30 |
| 142.0 | 33 |
| 135.7 | 59 |
| 135.0 | 65 |
| 128.9 | 54 |
| 119.9 | 53 |
| 117.2 | 27 |
| 89.4 | 18 |
| 81.5 | 17 |
| 56.3 | 23 |
| 50.2 | 100 |
| 41.5 | 98 |
| 34.8 | 57 |
| 30.2 | 68 |
| 22.4 | 38 |

Figure 9:
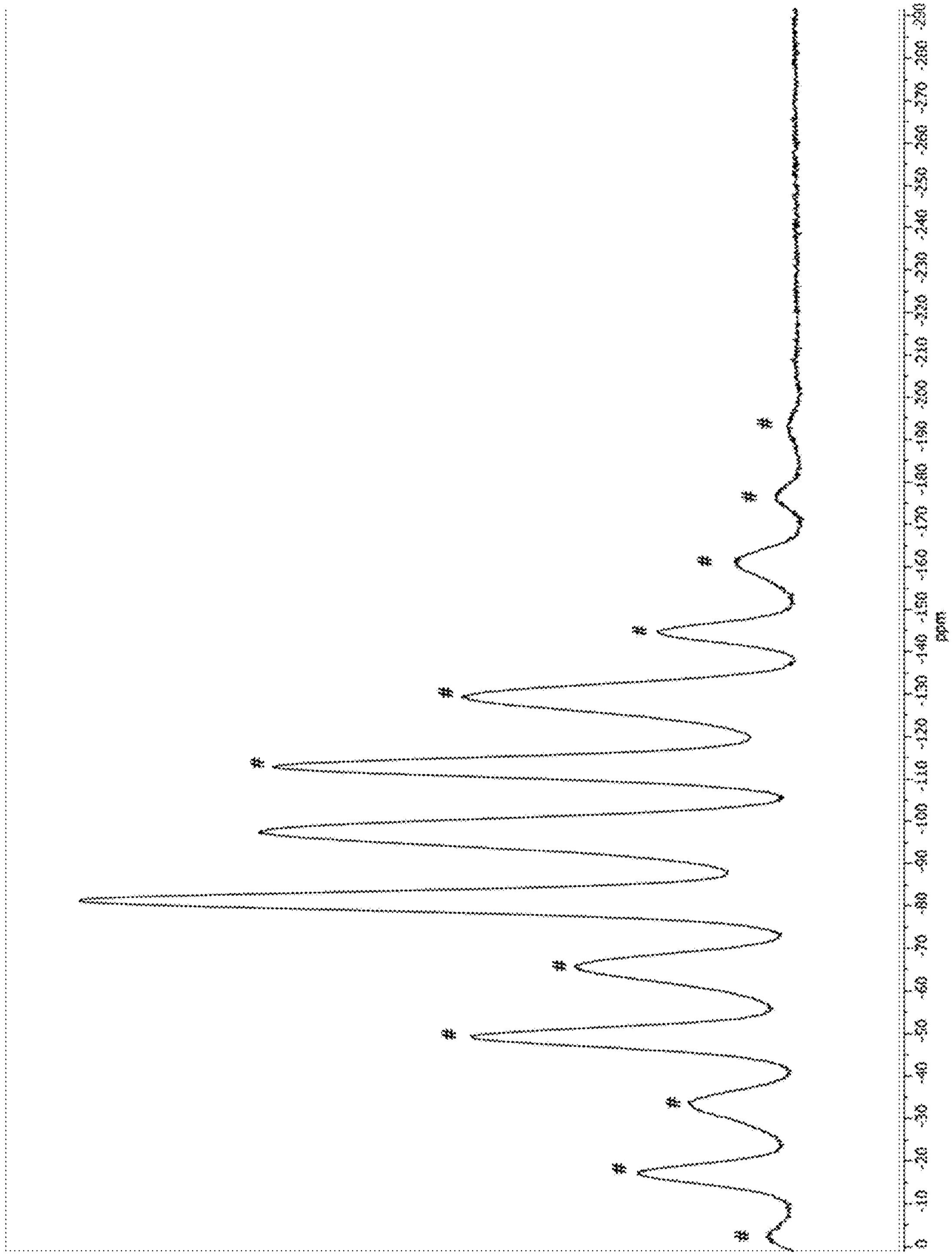
FIG. 9 shows $^{19}F$ solid state NMR spectrum of amorphous 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Form 3).
Figure 10:
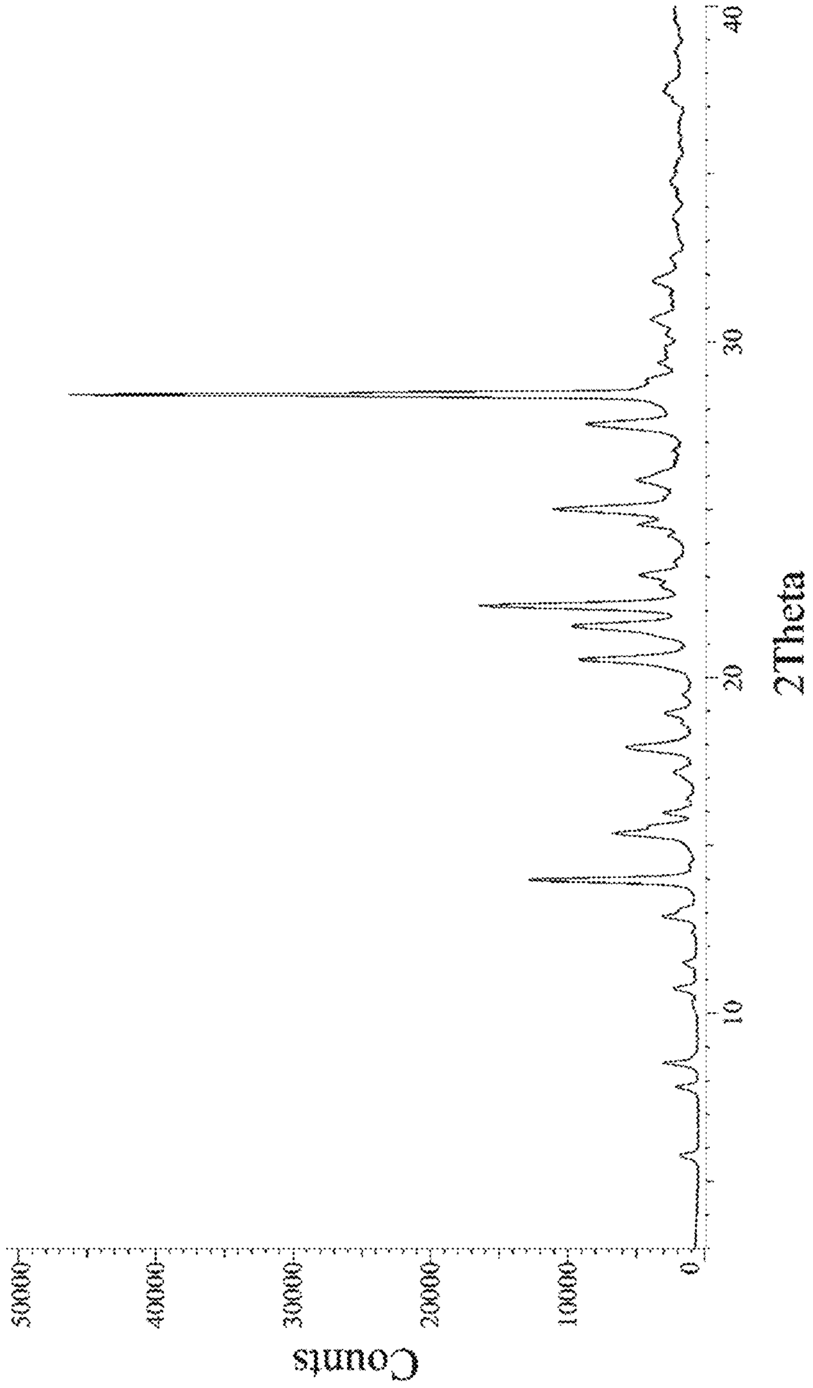
FIG. 10 shows the PXRD pattern of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)thieno[3,2-b]pyridine-3-carboxylic acid.

FIG. 9 also shows the $^{19}F$ solid state NMR spectrum of 7-(5-chloro-2-(3-(5-cyano-6-((1-(3,3-difluorocyclobutyl)piperidin-4-yl)(methyl)amino)-2-methyl-4-oxopyrido[3,4-d] pyrimidin-3(4H)-yl)prop-1-yn-1-yl)phenyl)-N-(methylsulfonyl)thieno[3,2-b]pyridine-3-carboxamide Form 3 amorphous, and Table 8 shows the $^{19}F$ solid state NMR peak list of the same form.

TABLE 8

| $^{19}F$ Chemical Shift (ppm) | Relative Intensity (%) |
|---|---|
| −81.4 | 100 |
| −97.4 | 75 |

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention.

The invention claimed is:

1. A crystalline form of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl) prop-1-yn-1-yl)phenyl)-N-(methylsulfonyl) thieno[3,2-b]pyridine-3-carboxamide hydrate, having a powder X-ray diffraction (PXRD) pattern comprising peaks at 2θ values of: 7.8, 6.4, and 5.2° 2θ±0.2° 2θ.

2. The crystalline form of claim 1, having a PXRD pattern further comprising a peak at a 2θ value of: 17.2° 2θ±0.2° 2θ.

3. The crystalline form of claim 1, having a Raman spectrum comprising wavenumber ($cm^{-1}$) values of: 1694 and 1680 $cm^{-1}$±2 $cm^{-1}$.

4. The crystalline form of claim 1, having a $^{13}C$ solid state NMR spectrum comprising resonance (ppm) values of: 47.3, 125.4, and 153.6 ppm±0.2 ppm.

5. The crystalline form of claim 1, having a 1° F. solid state NMR spectrum comprising resonance (ppm) values of: −93.2 and −80.4 ppm±0.2 ppm.

6. The crystalline form of claim 2, wherein said crystalline form is further characterized as having a $^{13}C$ solid state NMR spectrum comprising resonance (ppm) values of: 47.3, 125.4, and 153.6 ppm±0.2 ppm.

7. The crystalline form of claim 2, wherein said crystalline form is further characterized as having a $^{19}F$ solid state NMR spectrum comprising resonance (ppm) values of: −93.2 and −80.4 ppm±0.2 ppm.

8. A pharmaceutical composition comprising the crystalline form of claim 1, and a pharmaceutically acceptable carrier or excipient.

9. A method of treating breast cancer in a subject, the method comprising administering to the subject in need thereof, a therapeutically effective amount of the crystalline form of claim 1.

* * * * *